(12) United States Patent
Grinberg et al.

(10) Patent No.: US 12,201,454 B2
(45) Date of Patent: Jan. 21, 2025

(54) SYSTEM AND METHOD FOR DETECTING MEDICAL DEVICE DELIVERY TOOL POSITION

(71) Applicant: Medtronic, Inc., Minneapolis, MN (US)

(72) Inventors: Yanina Grinberg, Plymouth, MN (US); Ronald A. Drake, St. Louis Park, MN (US); Vincent P. Ganion, Blaine, MN (US); Kathryn Hilpisch, Cottage Grove, MN (US); Michael L Hudziak, Stillwater, MN (US); Michael Kemmerer, Victoria, MN (US); Alexander R. Mattson, St. Paul, MN (US); Pamela K. Omdahl, Andover, MN (US); Anthony W. Schrock, Ham Lake, MN (US); Kristina Yates, Wayzata, MN (US)

(73) Assignee: Medtronic, Inc., Minneapolis, MN (US)

( * ) Notice: Subject to any disclaimer, the term of this patent is extended or adjusted under 35 U.S.C. 154(b) by 918 days.

(21) Appl. No.: 17/016,470

(22) Filed: Sep. 10, 2020

(65) Prior Publication Data

US 2021/0077022 A1 Mar. 18, 2021

Related U.S. Application Data

(60) Provisional application No. 62/899,813, filed on Sep. 13, 2019.

(51) Int. Cl.
*A61B 5/00* (2006.01)
*A61B 5/06* (2006.01)

(52) U.S. Cl.
CPC ............ *A61B 5/686* (2013.01); *A61B 5/0015* (2013.01); *A61B 5/068* (2013.01); *A61B 5/6869* (2013.01)

(58) Field of Classification Search
CPC ......... A61B 5/283; A61B 5/29; A61B 5/6869; A61B 5/346–366; A61B 5/352;
(Continued)

(56) References Cited

U.S. PATENT DOCUMENTS 5,507,782 A 4/1996 Kieval et al.
7,751,882 B1 * 7/2010 Helland ................. A61B 5/318
607/9
(Continued)

FOREIGN PATENT DOCUMENTS

EP 3092943 A1 * 11/2016 ........... A61B 5/0022
WO WO-2006049539 A1 * 5/2006 ............... A61N 1/08
WO WO-2019050529 A1 * 3/2019 ............. A61B 5/061

OTHER PUBLICATIONS (PCT/US2020/050375) PCT Notification of Transmittal of the International Search Report and the Written Opinion of the International Searching Authority, Mailed Nov. 24, 2020, 10 pages.

*Primary Examiner* — Adam Z Minchella
*Assistant Examiner* — Davina E. Lee

(57) ABSTRACT

A medical system is configured to deliver an implantable medical device to a targeted implant site. The system may include a processor configured to receive a cardiac electrical signal and determine a feature of the cardiac electrical signal. The processor may be configured to determine a position of the delivery tool based on at least one feature of the cardiac electrical signal. The processor may detect a deployment position of the delivery tool in response to the cardiac electrical signal feature meeting criteria for detecting the deployment position.

28 Claims, 12 Drawing Sheets

(58) Field of Classification Search
CPC .... A61B 5/353; A61N 1/372; A61N 1/37518; A61N 1/3756; A61N 1/3956
See application file for complete search history.

(56) References Cited

U.S. PATENT DOCUMENTS

| | | | |
|---|---|---|---|
| 8,606,355 B1* | 12/2013 | Krause | A61N 1/36114 607/9 |
| 2001/0031927 A1* | 10/2001 | Werner | A61B 5/7203 600/523 |
| 2004/0147973 A1 | 7/2004 | Hauser | |
| 2006/0161223 A1* | 7/2006 | Vallapureddy | A61N 1/372 607/60 |
| 2008/0243202 A1* | 10/2008 | Patangay | A61N 1/3627 607/27 |
| 2009/0264780 A1* | 10/2009 | Schilling | A61N 1/057 604/20 |
| 2011/0251660 A1 | 10/2011 | Griswold | |
| 2011/0251662 A1 | 10/2011 | Griswold et al. | |
| 2012/0065529 A1* | 3/2012 | Cholette | A61N 1/362 600/510 |
| 2012/0172892 A1* | 7/2012 | Grubac | A61N 1/05 606/129 |
| 2014/0148815 A1 | 5/2014 | Wenzel et al. | |
| 2015/0265341 A1* | 9/2015 | Koblish | A61B 18/1492 606/41 |
| 2018/0036035 A1* | 2/2018 | Ruijter | A61B 17/3468 |
| 2018/0117304 A1* | 5/2018 | Koop | A61N 1/372 |
| 2018/0140328 A1 | 5/2018 | Shuros et al. | |
| 2018/0168686 A1* | 6/2018 | Jin | A61B 5/361 |
| 2018/0279897 A1* | 10/2018 | Eddy | A61B 5/287 |
| 2018/0280057 A1 | 10/2018 | Seifert et al. | |
| 2018/0289952 A1* | 10/2018 | Swerdlow | A61N 1/08 |
| 2019/0069794 A1* | 3/2019 | Bardy | A61B 5/35 |
| 2019/0083801 A1 | 3/2019 | Yang et al. | |
| 2020/0101279 A1 | 4/2020 | Drake et al. | |

* cited by examiner

SYSTEM AND METHOD FOR DETECTING MEDICAL DEVICE DELIVERY TOOL POSITION

REFERENCE TO RELATED APPLICATION

This application claims the benefit of U.S. Patent Application No. 62/899,813, filed provisionally on Sep. 13, 2019 and incorporated herein by reference in its entirety.

TECHNICAL FIELD

This disclosure relates to a medical device system and method for detecting a deployment position of a delivery tool configured to deliver an implantable medical device to an implant site within a subject's body.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscles, nerves, brain, stomach or other organs or tissue of a patient. Some medical devices may employ one or more electrodes for the delivery of therapeutic electrical signals to such organs or tissues and/or one or more electrodes for sensing intrinsic electrical signals within the patient that are generated by such organs or tissue. Similarly, some medical devices may additionally or alternatively include one or more other sensors for sensing physiological parameters of a patient.

For example, some medical devices may function as cardiac pacemakers or cardioverter-defibrillators that provide therapeutic electrical signals to the heart. The therapeutic electrical signals may include pulses for pacing, or shocks for cardioversion or defibrillation. In some examples, a medical device may sense intrinsic cardiac electrical signals attendant to depolarizations of the heart and thereby control delivery of therapeutic signals to the heart based on the sensed signals (or absence thereof). Upon detection of an abnormal rhythm, such as bradycardia, tachycardia, or fibrillation, an appropriate therapeutic electrical stimulation pulse or pulses may be delivered to restore or promote a relatively more normal heart rhythm. For example, in some cases, an implanted medical device may deliver pacing stimulation to the heart of the patient upon detecting tachycardia or bradycardia, and/or deliver cardioversion or defibrillation shocks to the heart upon detecting fibrillation.

A medical device may utilize one or more medical leads with one or more electrodes or other sensors for delivery of therapeutic electrical signals or sensing. For example, electrodes or sensors may be carried at a distal portion of a lead, and the proximal portion of the lead may be coupled to the medical device housing that contains circuitry such as pulse generation and/or sensing circuitry. Alternatively, an implanted medical device may function without a lead, such that the implantable medical device includes one or more electrodes on its outer housing to deliver therapeutic electrical pulses, and/or sense intrinsic electrical signals of patient. For example, a leadless cardiac pacemaker may be implanted within a heart chamber to sense intrinsic cardiac electrical signals produced by the heart and/or deliver therapeutic electrical stimulation pulses to the heart using electrodes carried by the housing of the leadless pacemaker.

SUMMARY

The techniques of this disclosure generally relate to a medical device system including a delivery tool for deploying an implantable medical device (IMD) at an implant site and methods for determining a deployment position of the delivery tool. In some examples, the IMD may be a leadless cardiac pacemaker or cardiac monitor configured to sense cardiac electrical signals produced by the patient's heart via housing-based electrodes. The delivery tool is configured to navigate a delivery pathway to a target implant site in or on the heart and deploy the IMD, which may include deploying a fixation member for anchoring the IMD at the implant site. A processor of a medical device system operating according to the techniques disclosed herein receives a cardiac electrical signal during the implantation procedure to detect a feature or a change in a feature of the cardiac electrical signal as it is advanced for determining a deployment position of the delivery tool relative to cardiac tissue for efficacious deployment of the IMD at the implant site. The deployment position of the delivery tool may be a position corresponding to wholly circumferential abutment of the delivery tool distal end face that promotes deployment and fixation of the IMD for optimal operational positioning and fixation of the IMD relative to the cardiac tissue at the implant site. In various examples, a cardiac electrical signal including cardiac event signal features attendant to myocardial depolarization may be displayed and or analyzed to detect a feature, or a relative change in a feature, of the cardiac electrical signal that meets criteria for determining a deployment position of the delivery tool. The IMD may be deployed from the delivery tool upon determining a deployment position of the delivery tool.

In one example, the disclosure provides a medical device including a processor configured to receive a cardiac electrical signal that includes cardiac event signals attendant to depolarizations of cardiac tissue, determine at least one feature of the cardiac electrical signal and determine that the at least one feature meets criteria for detecting a deployment position of a delivery tool. The delivery tool is configured to deploy an implantable medical device (IMD) at an implant site and is configured to retain the IMD as a distal end face of the delivery tool is advanced to the implant site. The processor is configured to generate an output in response to determining that the at least one feature meets the criteria for detecting the deployment position. The device may include a memory configured to store the output.

In another example, the disclosure provides a method, including determining at least one feature of a cardiac electrical signal that includes cardiac event signals attendant to depolarizations of cardiac tissue, determining that the at least one feature meets criteria for detecting a deployment position of a delivery tool configured to deploy an IMD at an implant site. The delivery tool is configured to retain the IMD as a distal end face of the delivery tool is advanced to the implant site. The method may further include deploying the IMD from the delivery tool in response to determining that the criteria are met.

In yet another example, the disclosure provides an implantable medical device system including a processor configured to receive a cardiac electrical signal that includes cardiac event signals attendant to depolarizations of cardiac tissue and generate an output based on the cardiac electrical signal. The system further includes a display unit configured to, in response to the output, generate a visual representation of changes in the cardiac event signals attendant to depolarizations of the cardiac tissue as a delivery tool is advanced to a deployment position. The delivery tool is configured to retain an IMD as the delivery tool is advanced to an implant site and facilitate deployment of the IMD at the implant site.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
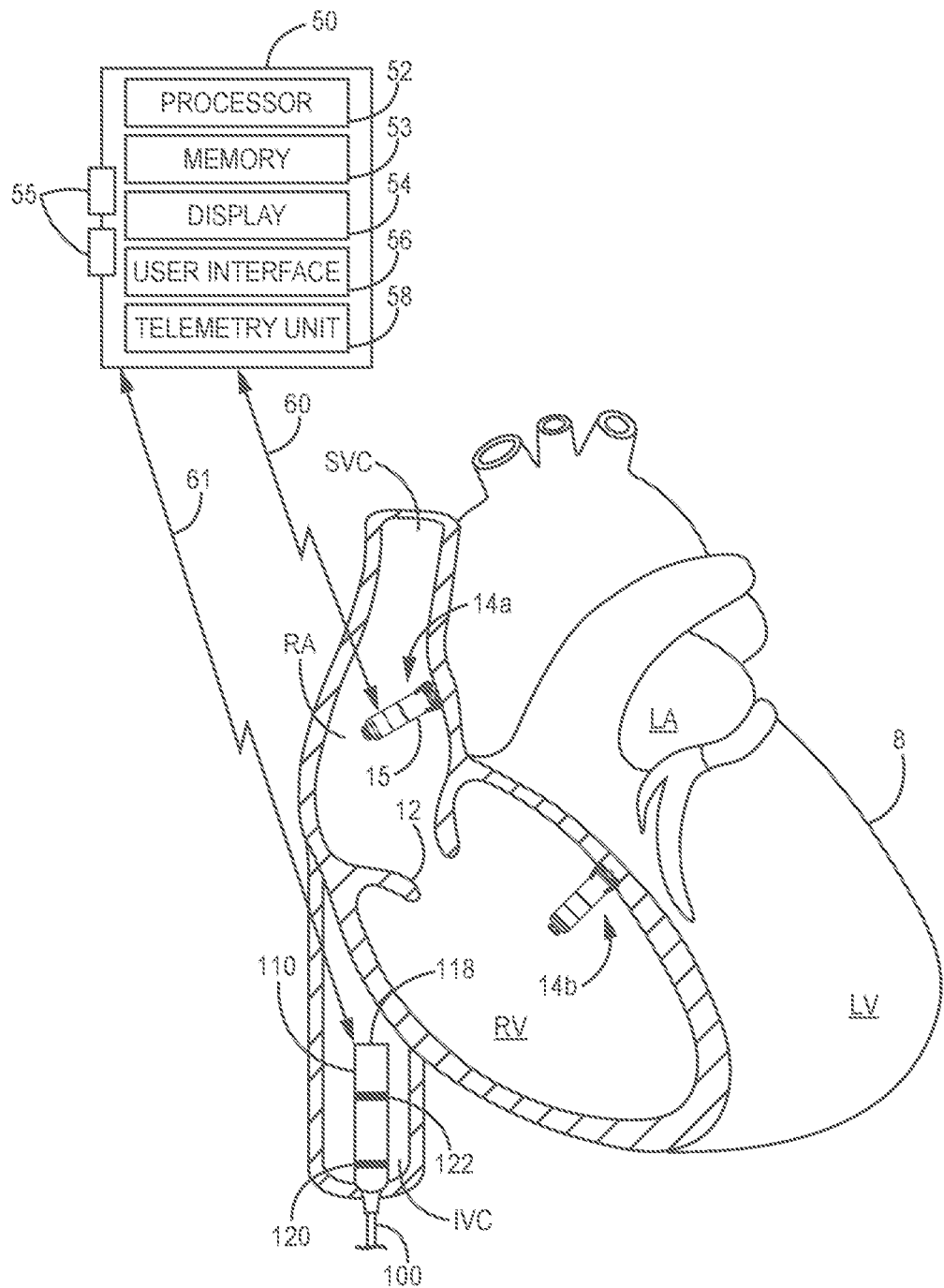
FIG. 1 is a conceptual diagram illustrating a medical device system that may be used to detect a deployment position of an IMD delivery tool according to one example.

Aspects of this disclosure relate to methods, devices and systems for delivering an implantable medical device (IMD) to a target site in a patient and verifying positioning of a delivery tool for efficacious deployment of the IMD at the target site. Once navigated to the target site, the IMD may be deployed from the delivery tool and secured to the target site by a fixation member. The delivery tool may include a navigable elongated member (e.g., a catheter) and a receptacle at a distal end of the elongated member for retaining the IMD during navigation to the implant site. The system may be configured to receive a cardiac electrical signal and display the cardiac electrical signal including features indicative of a deployment position of the delivery tool. In some examples the system may detect a deployment position of the delivery tool based on an analysis of a cardiac electrical signal. A cardiac electrical signal feature and/or a change in a cardiac electrical signal feature indicative of the deployment position may be detected by a processor, which may generate a deployment position detection output to a memory indicating that the delivery tool is in contact with the target implant site for achieving reliable fixation of the IMD fixation member in the cardiac tissue at the target site while avoiding perforation through the heart wall. The output stored in the memory may be used by the medical device system to generate a user notification that the delivery tool is determined to be in a deployment position. For example, aspects of the methods, devices and systems disclosed herein may include receiving a cardiac electrical signal produced by the heart and displaying the cardiac electrical signal including changes in cardiac electrical signal features indicative of advancement of a delivery tool to a deployment position. In some examples, the techniques include analyzing the cardiac electrical signal to confirm adequate contact of a distal end face of the delivery tool against the target implant site for efficacious deployment of the IMD. In some examples, the efficacious deployment position of the delivery tool corresponds to wholly circumferential contact of a distal end face of the delivery tool with viable tissue at the target site.

The delivery tool and/or IMD may include a first electrode that is within a receptacle of the delivery tool or along a distal end face of the delivery tool during navigation to the target implant site. For example, the first electrode may be a housing-based electrode of the IMD, an electrode secured to an inner wall of the delivery tool receptacle (e.g., along a delivery tool surface that faces the IMD when the IMD is retained within the delivery tool receptacle), or an electrode secured to a distal end face of the delivery tool, e.g., on a distal end face of the receptacle that comes into contact with the cardiac tissue at the target implant site. The medical device system includes a second electrode that may be within the delivery tool receptacle during navigation to the implant site or outside the delivery tool receptacle. For example, the second electrode may be a second housing-based electrode carried by the IMD, an electrode secured to an inner or outer surface of the delivery tool, or an electrode placed cutaneously or subcutaneously during the implant procedure.

The medical device system includes circuitry configured to sense an intrinsic cardiac electrical signal produced by the patient's heart via the first and second electrodes and determine a feature of the cardiac electrical signal. The circuitry may detect a feature of the cardiac electrical signal or a change in the feature of the cardiac electrical signal during advancement and positioning of the delivery tool against the target implant site that indicates a deployment position of the delivery tool. The medical device system may include a display unit configured to generate an output in response to detection of the deployment position of the delivery tool to notify a user that the delivery tool is in position for deployment of the IMD and fixation member. The display unit may be configured to generate an output in response to detecting one or more other, non-deployment positions of the delivery tool during advancement of the IMD to the target implant site.

FIG. 1 is a conceptual diagram illustrating a medical device system 10 that may be used to detect a deployment position of an IMD delivery tool according to one example. System 10 includes an IMD, e.g., IMD 14*a* shown implanted within the right atrium (RA) and/or IMD 14*b* shown implanted within the right ventricle (RV) of heart 8, referred to herein generally as IMD 14. IMD 14 is configured to sense cardiac electrical signals produced by the patient's heart 8 and provide pacing therapy to heart 8 according to one example. IMD 14 may be a transcatheter intracardiac pacemaker which may be adapted for implantation within a heart chamber. For example, two possible implant locations of IMD 14 are shown in FIG. 1. One implant location is represented by IMD 14a shown implanted within the RA, and another implant location is represented by IMD 14b shown implanted within the RV of heart 8.

IMD 14a is shown implanted at a particular location along an endocardial wall of the RA but may be implanted at other target implant locations within or on the RA, e.g., along a RA lateral wall, RA septum or within the RA appendage. IMD 14b is shown implanted along the interventricular septal wall but may be implanted at other target locations, e.g., along the endocardial, lateral free wall or the RV apex. The techniques disclosed herein are not necessarily limited to a particular heart chamber or implant location within or on a heart chamber. For example, an IMD 14 (referring to either IMD 14A or IMD 14b) may be positioned along an endocardial or epicardial surface of the RA, RV, left ventricle (LV) or left atrium (LA).

IMD 14 includes a housing 15, which may be hermetically sealed, for enclosing circuitry that is configured to sense a cardiac electrical signal produced by heart 8. The sensing circuitry may be configured to generate an intracardiac electrogram (EGM) signal from the sensed cardiac electrical signal. The cardiac electrical signal may be sensed by IMD 14 using electrodes carried by the housing 15 of IMD 14, as described below. IMD 14 may be a cardiac pacemaker including a therapy delivery circuit enclosed by housing 15 capable of producing electrical stimulation pulses, e.g., pacing pulses, delivered to heart 8 via the electrodes on the outer housing 15 of IMD 14. In the example shown, IMD 14a may be deployed in the RA for sensing cardiac electrical signals, producing an RA EGM signal and delivering RA pacing pulses. IMD 14b may be deployed in the RV for sensing cardiac electrical signals, producing an RV EGM signal and delivering RV pacing pulses. Other circuitry that may be enclosed by housing 15 is described below in conjunction with FIG. 4.

Delivery tool 100 is configured to navigate transvenously to heart 8 to deliver IMD 14 to a target implant site, e.g., IMD 14a to an implant site within the RA or IMD 14b to an implant site within the RV. Delivery tool 100 may be advanced transvenously to approach the heart 8 inferiorly via the inferior vena cava (IVC) as shown and enter the RA for deployment of IMD 14a at an RA implant site. For a target implant site within the RV, delivery tool 100 may be advanced from the RA across the tricuspid valve 12 into the RV. In other examples, IMD 14 may be advanced into a heart chamber via the superior vena cava (SVC). As described below in conjunction with FIGS. 3A-3C, delivery tool 100 may include a receptacle 110 for retaining IMD 14 during navigation to the target implant site. Upon reaching the implant site, an EGM signal received using a combination of electrodes carried by IMD housing 15 and/or receptacle 110 is analyzed to detect tissue contact by the distal end face 118 of receptacle 110. Tissue contact and abutment of the distal end face 118 may cause a change in the EGM signal that is detectable as a deployment position of delivery tool 100. As such, delivery tool 100 may include one or more electrodes, e.g., electrode 120 and/or electrode 122, used for sensing the cardiac electrical signal used to detect the deployment position of delivery tool 100. Upon detection of a deployment position of delivery tool 100 against the implant site, based on analysis of a cardiac electrical signal, e.g., an EGM signal, sensed by the medical device system 10, IMD 14 may be deployed from the receptacle 110 to secure IMD 14 at the implant site by a fixation member.

IMD 14 and/or delivery tool 100 may be configured for bidirectional communication with an external device 50. For example, IMD 14 may be configured for wireless communication with external device 50 via a wireless communication link 60. Delivery tool 100 may communicate with external device 50 via a wired or wireless communication link 61. IMD 14 may sense cardiac electrical signals via housing-based electrodes, generate an EGM signal, and transmit the EGM signal and/or data or information derived therefrom, such as determination of a deployment position of delivery tool 100, to external device 50 via communication link 60 in some examples. Additionally or alternatively, delivery tool 100 may sense a cardiac electrical signal via one or more electrodes carried by delivery tool 100 or via a combination of a first electrode carried by IMD housing 15 and a second electrode carried by delivery tool 100. Delivery tool 100 may transmit the cardiac electrical signal to external device 50. As described in conjunction with FIG. 3B, delivery tool 100 may include a processing circuit for generating an intracardiac EGM signal from the sensed cardiac electrical signal and may transmit the EGM signal or data or information derived therefrom to external device 50.

Aspects of external device 50 may generally correspond to the external programming/monitoring unit disclosed in U.S. Pat. No. 5,507,782 (Kieval, et al.), hereby incorporated herein by reference in its entirety. External device 50 may be a programmer used by a clinician or other qualified user for programming operating parameters in IMD 14 and receiving data from IMD 14, such as EGM signals. External device 50 may be located in a clinic, hospital or other medical facility. IMD operating parameters, including sensing and therapy delivery control parameters may be programmed into IMD 14 using external device 50.

External device 50 may include a processor 52, memory 53, display unit 54, user interface 56 and telemetry unit 58. Processor 52 controls external device operations and may process and analyze data and signals received from IMD 14. Display unit 54, which may include a graphical user interface, displays data, signals and/or other information to a user for reviewing IMD operation and programmed parameters as well as cardiac electrical signals retrieved from IMD 14. Data obtained from IMD 14 via communication link 60 may be displayed on display 54. For example, a clinician may view cardiac electrical signals received from IMD 14 and/or delivery tool 100 and may display results of cardiac electrical signal analysis performed by a processor of IMD 14, delivery tool 100 and/or external device processor 52 for determining a position of delivery tool 100 as described herein. Display unit 54 may be configured to generate a visual representation of a cardiac electrical signal and may generate a visual and/or audible output in response to detection of a deployment position of delivery tool 100. Accordingly, display unit 54 may include a screen such as a liquid crystal display, light emitting diode(s), speaker or other components for generating a visual and/or audible output to signal to a user that the deployment position has been detected.

Processor 52 executes instructions stored in memory 53 and may output data to memory 53. Processor 52 may include any one or more of a microprocessor, a controller, a digital signal processor (DSP), an application specific integrated circuit (ASIC), a field-programmable gate array (FPGA), or equivalent discrete or analog logic circuitry. In some examples, processor 52 may include multiple components, such as any combination of one or more microprocessors, one or more controllers, one or more DSPs, one or more ASICs, or one or more FPGAs, as well as other discrete or integrated logic circuitry. The functions attributed to processor 52 herein may be embodied as software, firmware, hardware or any combination thereof.

Memory 53 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 53 may be configured to store instructions executed by processor 52 for analyzing signals received from IMD 14 and/or delivery tool 100 for detecting a deployment position of delivery tool 100. Memory 53 may store output from processor 52 for use in generating a user notification or display of a determined position of delivery tool 100, which may correspond to an IMD deployment position or a non-deployment position notification.

User interface 56 enables a user to interact with external device 50 to initiate an implant or telemetry session with IMD 14 (and delivery tool 100 in some examples) for retrieving data from and/or transmitting data to IMD 14, including programmable parameters for controlling IMD operations. User interface 56 may include a mouse, touch screen, key pad or the like to enable a user to interact with external device 50 to initiate a telemetry session with IMD 14 for retrieving data from and/or transmitting data to IMD 14, including programmable parameters for controlling cardiac event sensing and therapy delivery. A clinician may use user interface 56 to send and receive commands to IMD 14 via external device 50. Typically, user interface 56 includes one or more input devices and one or more output devices, including display unit 54. The input devices of user interface 56 may include a communication device such as a network interface, keyboard, pointing device, voice responsive system, video camera, biometric detection/response system, button, sensor, mobile device, control pad, microphone, presence-sensitive screen, touch-sensitive screen (which may be included in display unit 54), network, or any other type of device for detecting input from a human or machine.

The one or more output devices of user interface 56 may include a communication unit such as a network interface, sound card, video graphics adapter card, speaker, presence-sensitive screen, one or more USB interfaces, video and/or audio output interfaces, or any other type of device capable of generating tactile, audio, video, or other output. Display unit 54 may function as an input and/or output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In other examples, user interface 56 may produce an output to a user in another fashion, such as via a sound card, video graphics adapter card, speaker, presence-sensitive screen, touch-sensitive screen, one or more USB interfaces, video and/or audio output interfaces, or any other type of device capable of generating tactile, audio, video, or other output. In some examples, display unit 54 is a presence-sensitive display that may serve as a user interface device that operates both as one or more input devices and one or more output devices.

Telemetry unit 58 includes a transceiver and antenna configured for bidirectional communication with a telemetry circuit included in IMD 14 (and/or delivery tool 100) and is configured to operate in conjunction with processor 52 for sending and receiving data relating to IMD functions via communication link 60. Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including cardiac electrical signals or associated data derived therefrom, results of device diagnostics, and histories of detected cardiac rhythms, delivered therapies, etc. may be retrieved from IMD 14 by external device 50 following an interrogation command.

External device 50 may receive data from delivery tool 100 via communication link 61. Communication link 61 may be wired or wireless, established using any of the examples given above. For example, a cardiac electrical signal or data derived therefrom may be transmitted from delivery tool 100 to processor 50 via telemetry unit 58 for analysis and determination of the position of delivery tool 100 during an implant procedure. In some examples, communication between delivery tool 100 and external device 50 is not required. For example, IMD 14 may sense a cardiac electrical signal and processing circuitry, included in IMD 14 and/or processor 52, may detect the position of delivery tool 100. External device 50 may generate an output stored in memory 53 which may be presented to a user via display unit 54 or user interface 56 indicating the detected position of delivery tool 100.

In some examples, external device 50 includes external ports 55 adapted for electrical connection to electrical leads carrying electrodes, which may be placed on the patient for sensing ECG signals during an implant procedure. As described below, a clinician may observe pacing artifact or a specified pacing rate as an indication that the delivery tool is in a deployment position in some examples.

Figure 2A:
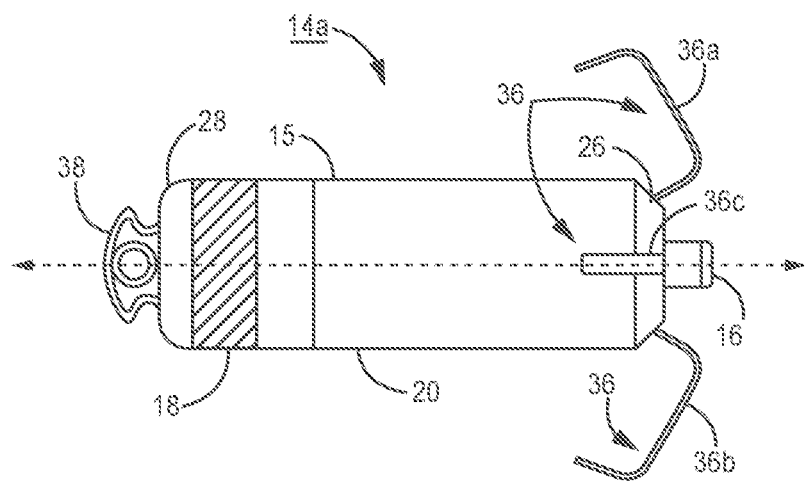
FIGS. 2A and 2B are conceptual diagrams of an IMD that may be delivered and deployed at a target implant site by a delivery tool.
Figure 2B:
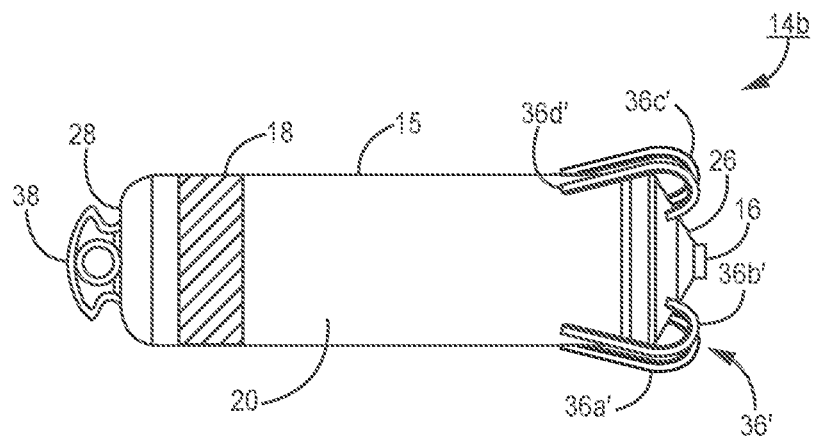

FIGS. 2A and 2B are conceptual diagrams of an IMD 14 that may be delivered and deployed at a target implant site by a delivery tool 100 as shown in FIG. 1. IMD 14, referring to either IMD 14a of FIG. 2A or IMD 14b of FIG. 2B, includes electrodes 16 and 18 spaced apart along the housing 15 of IMD 14 for sensing cardiac electrical signals and delivering pacing pulses. Housing 15 may be generally cylindrical to facilitate delivery via delivery tool 100. Housing 15 includes a lateral sidewall 20 extending from a distal end 26 to a proximal end 28 of housing 15. Electrode 16 is shown as a tip electrode positioned on the distal end 26 of IMD 14, and electrode 18 is shown as a ring electrode circumscribing lateral sidewall 20 along a mid-portion of housing 15, for example adjacent proximal end 28. Distal end 26 is referred to as "distal" in that it is expected to be the leading end, furthest from a clinician, as IMD 14 is advanced via delivery tool 100 to a targeted pacing site.

Electrodes 16 and 18 may be used as a cathode and anode pair for bipolar cardiac pacing and sensing. Electrodes 16 and 18 may be positioned at locations along IMD 14 other than the locations shown. In alternative embodiments, IMD 14 may include two or more ring electrodes, tip electrodes, and/or other types of electrodes exposed along housing 15 for delivering electrical stimulation to a patient's heart and sensing cardiac electrical signals. Electrodes 16 and 18 may be, without limitation, titanium, platinum, iridium or alloys thereof and may include a low polarizing coating, such as titanium nitride, iridium oxide, ruthenium oxide, platinum black among others.

Housing 15 is formed from a biocompatible material, such as a stainless steel or titanium alloy. In some examples, the housing 15 may include an insulating coating. Examples of insulating coatings include parylene, urethane, PEEK, or polyimide among others. The entirety of the housing 15 may be insulated, with only electrodes 16 and 18 uninsulated. Distal tip electrode 16 may serve as a cathode electrode and be coupled to internal circuitry, e.g., a pacing pulse generator and cardiac electrical signal sensing circuitry, enclosed by housing 15 via an electrical feedthrough crossing housing 15. Electrode 18 formed along an electrically conductive portion of housing 15 may serve as a return anode during pacing and sensing. Electrode 18 may be formed as a conductive portion of housing 15 when housing 15 is formed as an electrically conductive metal. In other examples, the entire periphery of the housing 15 may function as an electrode that is electrically isolated from tip electrode 16, instead of providing a localized ring electrode such as anode electrode 18. Distal tip electrode 16 and ring electrode 18 may be used to sense a cardiac electrical signal by sensing circuitry enclosed by housing 15 for generating an intracardiac EGM signal and detecting a position of the delivery tool 100 during advancement of IMD 14 to the target implant site.

Housing 15 encloses electronic circuitry for sensing cardiac signals, producing pacing pulses and controlling therapy delivery and other functions of IMD 14 as described below in conjunction with FIG. 3. Housing 15 further encloses a battery, which may be provided as a battery subassembly which provides power to a sensing, pacing and control electronics subassembly.

IMD 14 may include a fixation member 36. As represented by FIGS. 2A and 2B, the fixation member 36 of IMD 14a and the fixation member 36' of IMD 14b may be adapted for deployment and reliable fixation according to an intended implant site. For example, IMD 14a may be intended for implantation within an atrial chamber, and IMD 14b may be intended for implantation within a ventricular chamber as shown in FIG. 1. Because the atrial wall has different properties than the ventricular wall, notably the wall thickness, the fixation members 36 and 36' may have different shapes, lengths, curvature stiffness or other features selected to provide reliable advancement into the targeted cardiac tissue and chronic fixation of the IMD at the implant site. Fixation member 36 of IMD 14a is shown in FIG. 2A to include multiple tines 36a, 36b, and 36c (with a fourth fixation tine not visible in the view of FIG. 2A), collectively referred to as fixation member 36, to secure IMD 14a to patient tissue, e.g., by actively engaging with the atrial myocardial tissue, atrial pectinate, or the inner tip of the atrial appendage. Fixation member 36' of IMD 14b is shown in FIG. 2B to include multiple fixation tines 36a', 36b' 36c' and 36d' (collectively referred to as fixation member 36') configured for engaging the ventricular endocardium or ventricular trabeculae. The tines of fixation member 36 or 36' are configured to anchor IMD 14 to position tip electrode 16 against or in operative proximity to a targeted tissue site for sensing cardiac signals and/or delivering therapeutic electrical stimulation pulses. Fixation member 36 may correspond to the fixation member having multiple fixation tines as generally disclosed in commonly-assigned, U.S. Pat. No. 9,775,982 (Grubac, et al.), hereby incorporated herein by reference in its entirety. While fixation members 36 and 36' are shown having four fixation tines 36a-d (as best seen in FIG. 2B), fixation member 36 or 36' may include two or more tines extending from IMD distal end 26. In various examples, fixation member 36 may include one or more curved tines, angled tines, helical screw-in tines, hooked tines, barbed tines or other types of tines or combinations thereof that are shaped to engage with the cardiac tissue to securely anchor IMD 14 at the implant site.

The techniques disclosed herein provide detection of a deployment position of delivery tool 100, e.g., corresponding to firm tissue contact of delivery tool distal face 118 (FIG. 1), to promote sufficient depth of engagement of the fixation member 36 with the cardiac tissue at the implant site upon deployment of IMD 14 from the delivery tool receptacle 110. Secure engagement of each tine 36a-36d at a sufficient tissue depth reduces the likelihood of dislodgment of the IMD 14 over time. An implanting physician may not have tactile feedback or a view of the delivery tool distal face 118 to be confidant when the delivery tool distal face 118 is advanced against cardiac tissue in a manner that IMD 14 may be deployed and securely anchored by fixation member 36. By detecting a deployment position of the delivery tool in response to cardiac electrical signal changes that occur upon tissue contact and abutment of delivery tool distal face 118 against the cardiac tissue, a user operating delivery tool 100 is less likely to make errors in deploying IMD 14 that could result in inadequate fixation or dislodgment of IMD 14 from the implant site. The techniques for determining a deployment position of a delivery tool as disclosed herein promote sufficient cardiac tissue engagement and depth of the fixation member 36 to reduce the likelihood of IMD shifting or dislodgement. The disclosed techniques for detecting a deployment position of a delivery tool may be used in conjunction with a variety of types of fixation members and are not necessarily limited to use with a fixation member that includes only curved or angled tines such as the examples shown in FIGS. 2A and 2B.

IMD 14 may include a delivery tool interface 38. Delivery tool interface 38 may be located on the proximal end 28 of IMD 14 and is configured to connect to the delivery tool 100 used to position IMD 14 at the target implant site. Delivery tool interface 38 may be configured to mate with a delivery tool tether which may be electrically conductive to provide an electrically conductive pathway from delivery tool interface 38 to a proximal end of the delivery tool 100. Delivery tool interface 38 and a tether of delivery tool 100 may correspond to examples generally disclosed in U.S. Patent Application No. 2018/0280057 A1 (Seifert, et al.), incorporated herein by reference in its entirety. Delivery tool interface 38 may be electrically coupled (or electrically contiguous with) proximal ring electrode 18. In this way, a delivery tool tether electrically coupled to delivery tool interface 38 may provide electrical connection of proximal ring electrode 18 with the proximal end of the delivery tool 100 so that ring electrode 18 may be used as the one electrode enclosed within the delivery tool receptacle 110 for sensing a cardiac electrical signal for detecting the delivery tool position. Ring electrode 18 may be paired with a second electrode carried by the delivery tool 100 or placed cutaneously or subcutaneously on the patient in some examples. In other examples, the IMD electrodes 16 and 18 are used as a sensing electrode pair for sensing a cardiac electrical signal that may be used for detecting a delivery tool position.

Figure 3A:
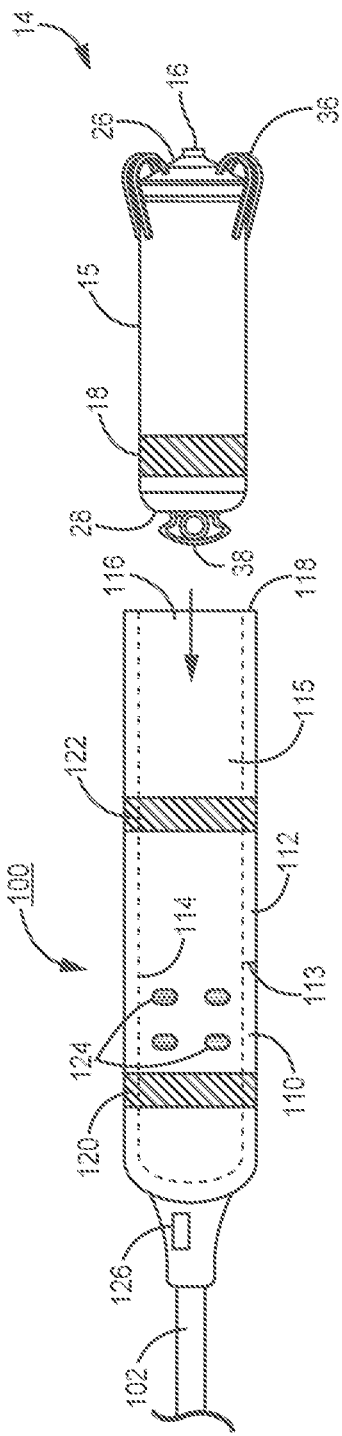
FIG. 3A is a conceptual diagram of a distal portion of a delivery tool and IMD according to one example.

FIG. 3A is a conceptual diagram of a distal portion of delivery tool 100 and IMD 14 according to one example. Delivery tool 100 includes an elongated body 102 coupled to an IMD receptacle 110. Elongated body 102 may be a steerable or navigable body including a guide wire, stylet, tether or other steering mechanism(s) to steer the receptacle 110 to a target implant site, e.g., via a transvenous pathway.

Receptacle 110 is configured to receive IMD 14 and retain IMD 14 within an open lumen 115 of receptacle 110 during navigation to the target implant site. Receptacle 110 has an outer wall 112 and inner wall 114 separated by a wall thickness 113 such that inner wall 114 defines the open lumen 115. Receptacle 110 receives IMD 14 through a distal opening 116 of receptacle 110. Distal opening 116 is defined by a circumferential distal end face 118 of receptacle 110.

Receptacle 110 may include one or more apertures 124 extending through wall thickness 113 from outer wall 112 to inner wall 114 to provide an electrically conductive pathway to ring electrode 18 of IMD 14 when IMD 14 is retained within receptacle 110. In some examples, one or more apertures 124 are provided at a location that is approximately aligned with ring electrode 18 along the longitudinal length of receptacle 110 when IMD 14 is fully retracted within receptacle 110 (see FIG. 3C). In some examples, a single aperture may be provided. In other examples, multiple apertures may be spaced apart circumferentially around receptacle 110. For example, two apertures may be on opposing sides of receptacle 110. In other examples, three, four or more apertures may be provided, spaced apart circumferentially and/or longitudinally along receptacle 110. For example, as shown in FIG. 3A, two rows of apertures may be provided spaced apart longitudinally from each other along receptacle 110. Each row may include multiple apertures spaced apart circumferentially around receptacle 110. Multiple rows of apertures may promote longitudinal alignment of at least one aperture with a ring electrode carried by IMD 14, e.g., ring electrode 18, when IMD 14 is retracted or advanced to different longitudinal positions within receptacle 110. Apertures 124 may provide a fluid pathway for blood through receptacle 110, e.g., through distal opening 116, lumen 115 and one or more apertures 124. By providing a fluid pathway, e.g., for blood flowing in a heart chamber, an electrically conductive pathway exists between an electrode within receptacle 110, which may be carried by IMD 14 or inner wall 114 of receptacle 110, and the cardiac tissue at the target implant site to enable sensing of the cardiac electrical signal by at least one electrode within the receptacle 110 as distal end face 118 is advanced toward and against the target implant site. In some examples, the fluid pathway extending through one or more apertures 124 provides an electrically conductive pathway between tip electrode 16 and ring electrode 18 carried by IMD 14 for enabling sensing of cardiac signals via IMD housing-based electrodes 16 and 18 while IMD 14 is retained within receptacle 110. The receptacle 110 with apertures 24 may correspond to any of the examples of a device cup with vent holes as generally disclosed in U.S. Patent Application No. 62/879,715, filed provisionally on Jul. 29, 2019, and subsequent non-provisional U.S. patent application Ser. No. 16/921,512, both incorporated herein by reference in their entirety.

Delivery tool 100 may optionally include one or more electrodes 120 and 122 to facilitate sensing of cardiac electrical signals during IMD 14 implantation. In some examples, one electrode 120 may be carried along the outer wall 112. Another electrode 122 may be carried along the inner wall 114 of receptacle 110. Electrode 120 along outer wall 112 may be used as the second electrode paired with the first electrode contained within receptacle 110 or on distal end face 118 for sensing a cardiac electrical signal for detecting delivery tool position. For example, one of IMD housing based electrodes 16 or 18 or electrode 122 on inner wall 114 may serve as a first electrode contained within receptacle 110 during IMD implantation and electrode 120 on outer wall 112 may serve as the second electrode paired with the first electrode for sensing a cardiac electrical signal used in determining delivery tool position. In other examples, either electrode 120 or 122 may be used as a second return electrode for acquiring a cardiac electrical signal in combination with the tip electrode 16 of IMD 14 or ring electrode 18 of IMD 14.

Figure 3B:
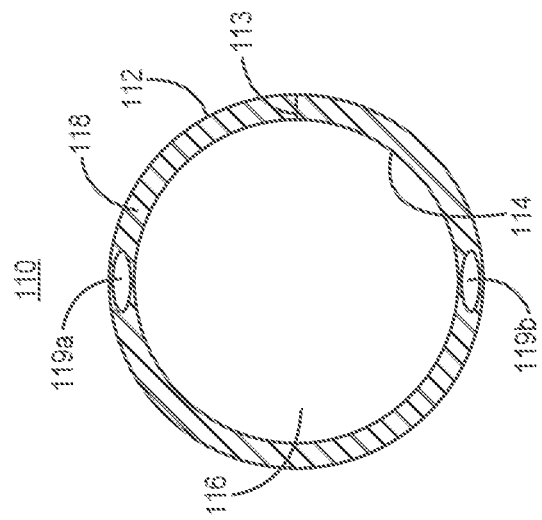
FIG. 3B is a distal end view of a delivery tool according to one example.

FIG. 3B is a distal end view of delivery tool receptacle 110. Distal end face 118 of receptacle 110 is defined by wall thickness 113 separating inner wall 114 from outer wall 112 at the distal end of receptacle 110. Distal end face 118 defines the distal opening 116 through which IMD 14 is received by receptacle 110. Receptacle 110 may include one or more electrodes 119a and 119b on distal end face 118 in some examples. Electrodes 119a and 119b may be electrically isolated and may be used as first and second electrodes of the sensing electrode pair for receiving the cardiac electrical signal used for detecting the position of delivery tool 100. One of electrodes 119a or 119b may be used as the first electrode and another electrode, e.g., IMD housing-based electrode 18, one of electrodes 120 or 122, or a subcutaneous or cutaneously placed indifferent electrode may be used as the second electrode for sensing the cardiac electrical signal. In other examples, electrodes 119a and 119b may be electrically coupled to serve as a single electrode on distal end face 118 and used as the first electrode paired with a second electrode, e.g., IMD housing-based electrode 18, one of electrodes 120 or 122 or a cutaneously or subcutaneously placed indifferent electrode, for sensing a cardiac electrical signal during advancement of delivery tool 100.

While two electrodes 119a and 119b are shown on distal end face 118, one, two or more than two electrodes may be located on distal end face 118. The two electrodes 119a and 119b are shown diametrically opposed, e.g., 180 degrees apart, along distal end face 118. Two or more electrodes on distal end face 118 may be located at other inter-electrode distances, e.g., at varying angles or arc lengths relative to one another, along the circumferential distal end face 118. When two or more electrically isolated electrodes 119a and 119b are located on distal end face, two cardiac electrical signals may be sensed for verifying the position of delivery tool 100. For example, electrode 119a may be paired with either electrode 120 or 122 to sense one cardiac electrical signal and electrode 119b may be paired with either electrode 120 or 122 to sense a second cardiac electrical signal. Both cardiac electrical signals may be analyzed by processing circuitry of the medical device system for detecting the delivery tool position using the techniques disclosed herein.

When one or more electrodes 119a, 119b, 120 and/or 122 are carried by receptacle 110, each respective electrode is coupled to an elongated, insulated electrical conductor extending through a lumen of elongated body 102 extending to a proximal end of delivery tool 100. Receptacle 110 may include one or more lumens extending through wall thickness 113 to delivery tool elongated body 102. An electrical conductor may extend through each lumen to a respective electrode 119a and 119b to enable electrodes 119a and 119b to be electrically coupled to cardiac electrical signal sensing circuitry. Elongated body 102 may include one or more lumens for carrying electrically isolated conductors from each of electrodes 119a, 119b, 120 and 122 to provide electrical connection to the proximal end of the delivery tool 100. A cardiac electrical signal received via a sensing electrode pair that includes one or more of electrodes 119a, 119b, 120, 122 and/or IMD ring electrode 18 may be passed to an external device, e.g., external device 50 (FIG. 1), for generating a display of the EGM signal from the sensed cardiac electrical signal and, in some examples, analyzing the EGM signal by processor 52 of external device 50 for detecting the position of delivery tool 100.

Detection of the position of delivery tool 100 includes detecting abutment of distal end face 118 against cardiac tissue at a target implant site in some examples. Abutment of distal end face 118 refers to complete circumferential contact of distal end face 118 with cardiac tissue. Abutment of distal end face 118 is desired before deployment of IMD 14 out of receptacle 110 in order to promote reliable fixation of IMD 14 via all tines of fixation member 36 and to promote reliable, operational contact between tip electrode 16 and the cardiac tissue at the target site. In some instances, distal end face 118 may be in contact with the cardiac tissue at an angle such that only partial contact between distal end face 118 and the cardiac tissue is made rather than full circumferential contact of distal end face 118 with adjacent tissue. Detecting a deployment position of delivery tool 100 may correspond to firm contact between the cardiac tissue and the wholly circumferential distal end face 118 to an extent that is acceptable for IMD deployment and fixation based on an analysis of the cardiac electrical signal.

Additionally or alternatively, determination of a deployment position of delivery tool 100 may be based on an amplitude of a P-wave (for atrial implantation) or R-wave (for ventricular implantation) falling within an acceptable range. The amplitude of the P-wave or R-wave may indicate a viable tissue site for cardiac pacing delivery. The amplitude of the P-wave or R-wave may be required to fall within a specified range to promote deployment of the IMD 14 at an implant site having a heart chamber wall thickness that promotes reliable fixation of fixation member 36. A high P-wave amplitude, for example, may be indicative of a relatively thick portion of the atrial wall that may be too stiff for piercing of the tissue by the tines of fixation member 36. Too low of P-wave amplitude may be indicative of a necrotic portion of the atrial wall where pacing may be ineffective or a relatively thin portion of the atrial wall that may result in perforation of the wall by fixation member 36. As such, a deployment position of delivery tool 100 may be determined based on the amplitude of the P-wave (or R-wave) of the cardiac electrical signal being greater than a specified minimum and/or less than a specified maximum amplitude.

A sustained, characteristic cardiac electrical signal feature that occurs with continuous circumferential abutment of distal end face 118 against the cardiac tissue or a change in one or more cardiac electrical signal features that occurs upon establishing continuous circumferential abutment of distal end face 118 against the cardiac tissue that is not intermittent due to motion of the beating heart, is indicative of a deployment position of the delivery tool. In some instances, abutment to the extent acceptable for IMD deployment may result in some bulging of the cardiac tissue around the distal end face 118. However, excessive pressure of distal end face 118 against the cardiac tissue may be avoided by detecting abutment at the time that distal end face 118 is in full contact with the tissue, thereby avoiding over advancement of the delivery tool 100, which may cause undue tissue injury by the distal end face 118 and/or perforation of the cardiac wall by fixation member 36 upon deployment.

Detection of the position of delivery tool 100 during advancement to the target implant site may include detecting immersion of distal end face 118 in a blood pool and/or detection of light and/or non-circumferential contact between the cardiac tissue and distal end face 118. For instance, immersion in the blood pool of a cardiac chamber may be detected prior to detecting abutment of the distal end face 118 based on cardiac signal features. Examples of cardiac signal features and changes in cardiac signal features that may occur with changing position of the delivery tool 100 are described below in conjunction with associated with FIGS. 6-8.

A processor of IMD 14 may be configured to detect the deployment position of delivery tool 100, based on an analysis of a cardiac electrical signal sensed via electrodes 16 and 18. IMD 14 may generate an output signal as a deployment position notification signal to notify a user that the IMD 14 may be deployed from the delivery tool 100. Since IMD 14 may be in a relatively deep implant position, reception of telemetry signals transmitted from IMD 14 to external device 50 may be intermittent or poor under some circumstances. IMD 14 may be configured to transmit a deployment position notification signal as a radiofrequency (RF) or electromagnetic (EM) signal or a physical vibration of IMD 14 caused by driving a piezoelectric element included in IMD 14 as described below. Delivery tool 100 may include a sensor 126 for sensing a deployment position notification signal output from IMD 14.

Figure 3C:
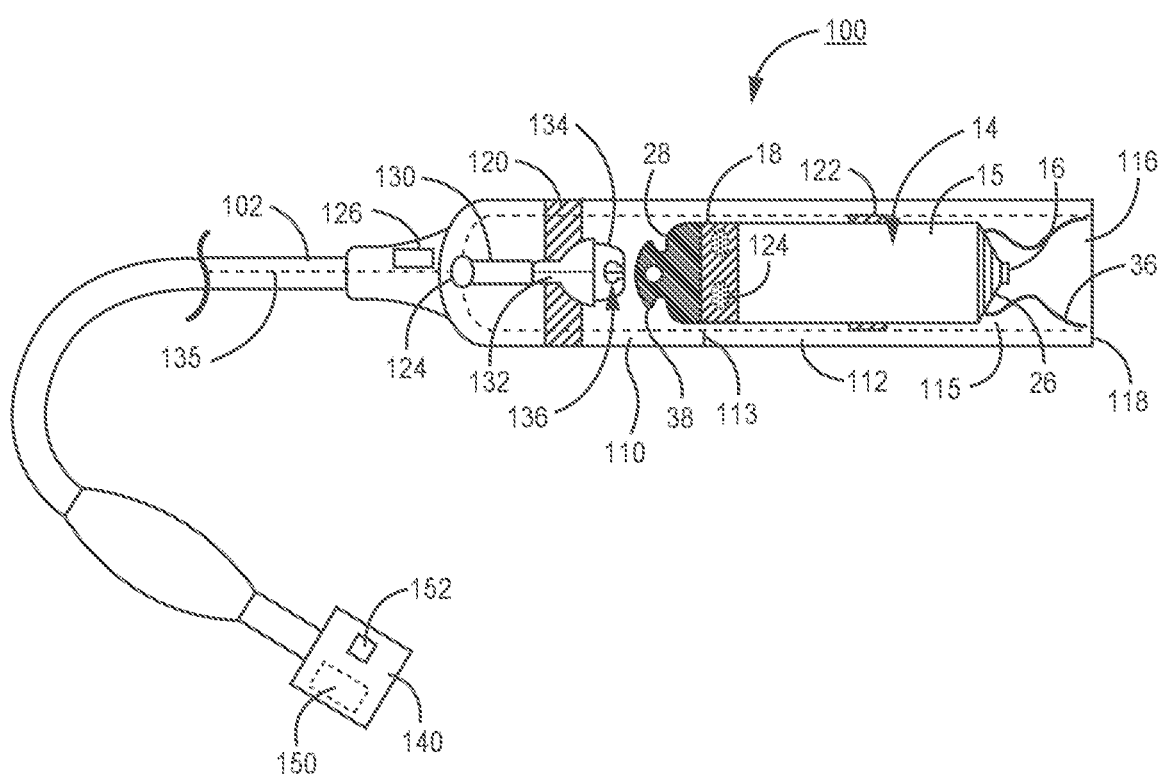
FIG. 3C is a conceptual diagram of a delivery tool with an IMD retained within the delivery tool according to one example.

Sensor 126 may therefore include an RF receiver, an EM receiver, or a piezoelectric, piezoresistive or capacitive accelerometer, or a microelectromechanical system (MEMS) sensor as examples. Sensor 126 may be configured to sense a deployment position notification signal output by IMD 14 and transmit a signal via a conductor extending through elongated body 102 from sensor 126 to sensing and processing circuitry 150 at the proximal end of delivery tool 100, as shown in FIG. 3C and described below. Sensing and processing circuitry 150, upon receipt of the deployment position notification signal from sensor 126, may generate a user notification output to alert the user that IMD 14 may be deployed. Examples of user notification output signals that may be generated by delivery tool 100 in response to sensor 126 detecting a deployment position notification signal from IMD 14 are described below in conjunction with FIG. 3C. While sensor 126 is shown along a transition portion between elongated body 102 and receptacle 110, other locations of sensor 126 are possible. Sensor 126 may be incorporated in delivery tool 100 at other locations or at distributed locations when more than one receiver or sensor is included in sensor 126, including within the wall thickness 113 of receptacle 110, along the outer wall 112 or inner wall 114 of receptacle 110, along elongated body 102 or in proximal hub 140.

FIG. 3C is a conceptual diagram of delivery tool 100 with IMD 14 retained within receptacle 110 according to one example. In FIG. 3C, IMD 14 is retained within receptacle 110 with the multiple tines of fixation member 36 held in an extended position within the confines of receptacle 110. As IMD 14 is advanced out of receptacle 110, e.g., after detecting abutment of delivery tool distal end face 118 against cardiac tissue, the distal tips of the tines of fixation member 36 pierce the cardiac tissue then flex back as IMD 14 is advanced further. The fixation member tines relax into the unconstrained, normally curved position as shown in FIG. 3A. After piercing the cardiac tissue then relaxing back into the curved position, each tine entraps cardiac tissue within the curved portion of the tine providing secure fixation of IMD 14 at the implant site. When delivery tool distal end face 118 is only lightly contacting the cardiac tissue or contacting the cardiac tissue at an angle upon deployment of IMD 14 from receptacle 110, the tines of fixation member 36 may not penetrate the cardiac tissue deeply enough to ensure secure engagement with the cardiac tissue and fixation of IMD 14 at the implant site and/or only a portion of the total number of tines, instead of all of the tines, may adequately engage with the cardiac tissue. When delivery tool 100 is over advanced against the cardiac tissue, the tines of fixation member 36 may penetrate too deeply, causing undue tissue injury at the implant site and/or perforation of the fixation member tines through the heart chamber wall. The techniques disclosed herein enable the IMD system 10 to detect abutment of delivery tool distal end face 118 against the cardiac tissue prior to deployment of IMD 14. Upon detecting abutment, an output may be generated to notify the user that a deployment position of the delivery tool 100 has been detected that promotes secure engagement with cardiac tissue by all of the tines of fixation member 36 while discouraging or avoiding over advancement and excessive pressure of distal end face 118 against the target implant site.

Elongated body 102 of delivery tool 100 may define a number of longitudinal lumens for a variety of purposes. For example, elongated body 102 may define one or more peripheral lumens for carrying electrical conductors extending proximally from electrodes 119*a*, 119*b*, 120, and 122, when included, and a central lumen configured to house deployment member 130 having a distal pushing cup 132 at the distal end of deployment member 130. Distal pushing cup 132 is configured to mate with IMD proximal end 28. Additionally, or alternatively, deployment member 130 may include a tether 134 that may be configured to engage with delivery tool interface 38 of IMD 14 for retaining, pushing, retracting, or otherwise retain or move IMD 14 relative to receptacle 110.

Deployment member 130 extends through elongated body 102 and is axially slidable within elongated body 102, e.g., along the longitudinal axis 135 of delivery tool 100. A clinician operating delivery tool 100 may advance deployment member 130 distally through elongated body 102 to advance pushing cup 132 into contact with IMD proximal end 28 and thereby impart a distal force on proximal end 28 of IMD 14. In this way, the clinician may deploy IMD 14 from receptacle 110, through distal opening 116, after determining a deployment position of delivery tool 100, e.g., associated with detecting abutment of delivery tool distal end face 118 against cardiac tissue based on a sensed cardiac electrical signal.

In some examples, tether 134 includes a clamp 136 having opposing teeth configured to grasp delivery tool interface 138 of IMD 14. Tether 134 may be configured to be slideable within deployment member 130. Specifically, tether 134 may be configured to be longitudinally moveable within a lumen of deployment member 130, such that teeth of clamp 136 may open when extended out of the distal end of deployment member 130 (e.g., out of pushing cup 132) and actuated to close down on delivery tool interface 38 of IMD 14. Clamp 136 may be actuated (e.g., opened or closed) under the control of a clinician operating delivery tool 100. For example, a clinician may actuate clamp 136 open or closed from a control mechanism of deployment member 130 on or adjacent proximal hub 140. Though clamp 136 is shown as not engaging delivery tool interface 38 in FIG. 3C for purposes of clarity, it is to be understood that clamp 136 may engage delivery tool interface 38 until IMD 14 is securely fixed at the target implant site. Upon fixation at the target implant site, clamp 136 may be opened using proximal hub 140 to release delivery tool interface 38 from clamp 136. Deployment member 130 (including tether 134) may be retracted proximally within receptacle 110 and elongated body 102. Delivery tool 100 may then be withdrawn from the patient leaving IMD 14 securely fixed at the target implant site.

Tether 134 may be longitudinally slidable and rotatable within deployment member 130 and configured to provide torsional transfer from the proximal hub 140 to clamp 136. Clamp 136 may be closed around delivery tool interface 38 such that rotation of tether 134 causes rotation of IMD 14 in some examples, e.g., when IMD fixation member 36 includes a helical, screw-in tine that is rotated into the cardiac tissue at the target implant site.

In some examples, deployment member 130 is used to advance IMD 14 distally within receptacle 110 until the tines of fixation member 36 are advanced out of receptacle 110 and curve back toward their normally-relaxed position without engaging cardiac tissue, e.g., while the distal end face 118 is positioned within the blood pool of a heart chamber. The delivery tool 100 may then be advanced until abutment of the distal end face 118 is detected, corresponding to a deployment position of delivery tool 100. With IMD 14 partially advanced within receptacle 110, with fixation member 36 advanced out of receptacle 110, tip electrode 16 remains within receptacle 110 (or approximately flush with distal end face 118) but in closer proximity to the cardiac tissue than when the IMD 14 (and fixation member 36) is fully retracted within receptacle 110. Partial advancement within receptacle 110 to position distal tip electrode 118 in closer proximity to cardiac tissue for receiving the cardiac electrical signal may improve cardiac electrical signal quality such that discrimination of cardiac electrical signal features that indicate wholly circumferential abutment of the distal end face 118 against the cardiac tissue are reliably detected.

After detection of the deployment position of the delivery tool 100 based on the cardiac electrical signal, tether 134 may be retracted with clamp 136 still closed around delivery tool interface 38 to fully retract fixation member 36 back into receptacle 110. The deployment member 130 may then be advanced to deploy IMD 14 out of receptacle 110, and thereby deploy fixation member 36 to sufficiently engage with the cardiac tissue at the implant site. Clamp 136 may be opened using proximal hub 140 to release delivery tool interface 38 and delivery tool 100 may be withdrawn from the patient leaving IMD 14 in place.

In some examples, proximal hub 140 may include a sensing and processing circuit 150 configured to sense a cardiac electrical signal via a selected sensing electrode pair and detecting abutment of delivery tool distal end face 118 against cardiac tissue according to the techniques disclosed herein. Sensing and processing circuit 150 may therefore include a cardiac electrical signal sensing circuit, which may include an input filter and amplifier, an analog to digital converter, a bandpass filter, a rectifier, a peak detection and hold circuit, a comparator, sense amplifier or other cardiac event detection circuitry for sensing a cardiac electrical signal. In other examples, sensing and processing circuit 150 is configured to receive a signal passed from sensor 126 in response to sensor 126 sensing a deployment position notification signal transmitted by IMD 14. Sensing and processing circuit 150 may therefore include one or more microprocessor, controller, digital signal processor (DSP), application specific integrated circuit (ASIC), field-programmable gate array (FPGA), or equivalent discrete or analog logic circuitry configured to detect features of the sensed cardiac electrical signal and/or detect a signal from sensor 126 for determining a position of the delivery tool distal face 118 according to techniques disclosed herein.

Sensing and processing circuit 150 may include a memory for storing computer-readable instructions executed by a processor included in sensing and processing circuit 150 for determining a position of delivery tool distal end face 118 and generating an output in response to the determined position. The memory may be configured to receive and store an output signal generated by sensing and processing circuit 150 in response to determining a position of delivery tool 100. Sensing and processing circuit 150 may therefore include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), or other memory device.

Proximal hub 140 may further include a user interface 152 that generates user notification signals. User interface 152 may include a light emitting diode (LED), a speaker, and/or a buzzer or piezoelectric element generating a mechanical vibration, as examples, for generating a visual, audible and/or haptic notification to the user that a deployment position of delivery tool 100 is detected by way of a blinking LED, broadcast sound, and/or vibration as examples. The user interface 152 may generate a user notification signal in response to a deployment position detection signal output to memory of sensing and processing circuit 150. Sensing and processing circuit 150 and/or delivery tool user interface 152 may operate cooperatively with circuitry enclosed by IMD 14, described below, for detecting one or more positions of the delivery tool 100, including at least a deployment position corresponding to cardiac tissue abutment by delivery tool distal end face 118, and generating an output for notifying the clinician to deploy IMD 14. In other examples, proximal hub 140 may function mechanically as a delivery tool handle and actuation mechanism without including sensing and processing circuit 150 and/or user interface 152. In this case, signals from IMD 14 may be transmitted to external device 50 and user notification signals may be generated by display unit 54 of external device 50 to indicate detection of one or more positions of the delivery tool 100.

When included, sensing and processing circuit 150 of delivery tool 100 may receive a cardiac electrical signal from one or more electrodes carried by delivery tool 100 and/or from an electrode carried by IMD 10. For example, tether 134 may be electrically coupled to ring electrode 18 upon closure of clamp 136 around delivery tool interface 38. An electrical conductor may extend proximally from clamp 136 to proximal hub 140 to provide electrical connection of ring electrode 18 to sensing and processing circuit 150 or other sensing and processing circuitry, e.g., via connection to external device 50.

Sensing and processing circuit 150 may be configured to detect abutment of the delivery tool distal end face 118 against cardiac tissue according to the techniques disclosed herein. Sensing and processing circuit 150 may detect the deployment position of delivery tool 100 by receiving a deployment position detection signal from sensor 126, as described above, in response to IMD 14 transmitting a deployment position detection signal. Sensing and processing circuit 150 may alternatively detect the deployment position based on an analysis of a cardiac electrical signal received by sensing and processing circuit 150 from IMD electrode 18 (electrically coupled to clamp 136) and/or one or more electrodes carried by receptacle 110. Upon detecting the deployment position, sensing and processing circuit 150 may generate an output to user interface 152 to cause user interface to generate a user notification to deploy IMD 14.

Sensing and processing circuit 150 may cause user interface 152 to indicate to the clinician one or more positions of delivery tool distal end face 118, e.g., immersed in a heart chamber blood pool, light contact or touching with cardiac tissue, and/or wholly circumferential abutment against cardiac tissue corresponding to an IMD deployment position of delivery tool receptacle 110. Delivery tool user interface 152 may adjust an output signal to indicate detection of the deployment position, e.g., illuminate an light emitting diode, adjust from a red to green color of a light emitting diode, broadcast a sound by a speaker or adjust a broadcast sound from a low tone or beep to a relatively higher ding, and/or generate a light vibration that transitions to a stronger and/or intermittent vibration in response to detecting abutment of distal end face 118 against cardiac tissue. In other examples, user interface 152 may receive a telemetered signal from IMD 14 to cause user interface 152 to generate a predetermined output signal (visual, audible, and/or haptic) indicating a deployment position of delivery tool 100 as determined by circuitry enclosed within IMD 14, as further described in conjunction with FIG. 4 below.

Figure 4:
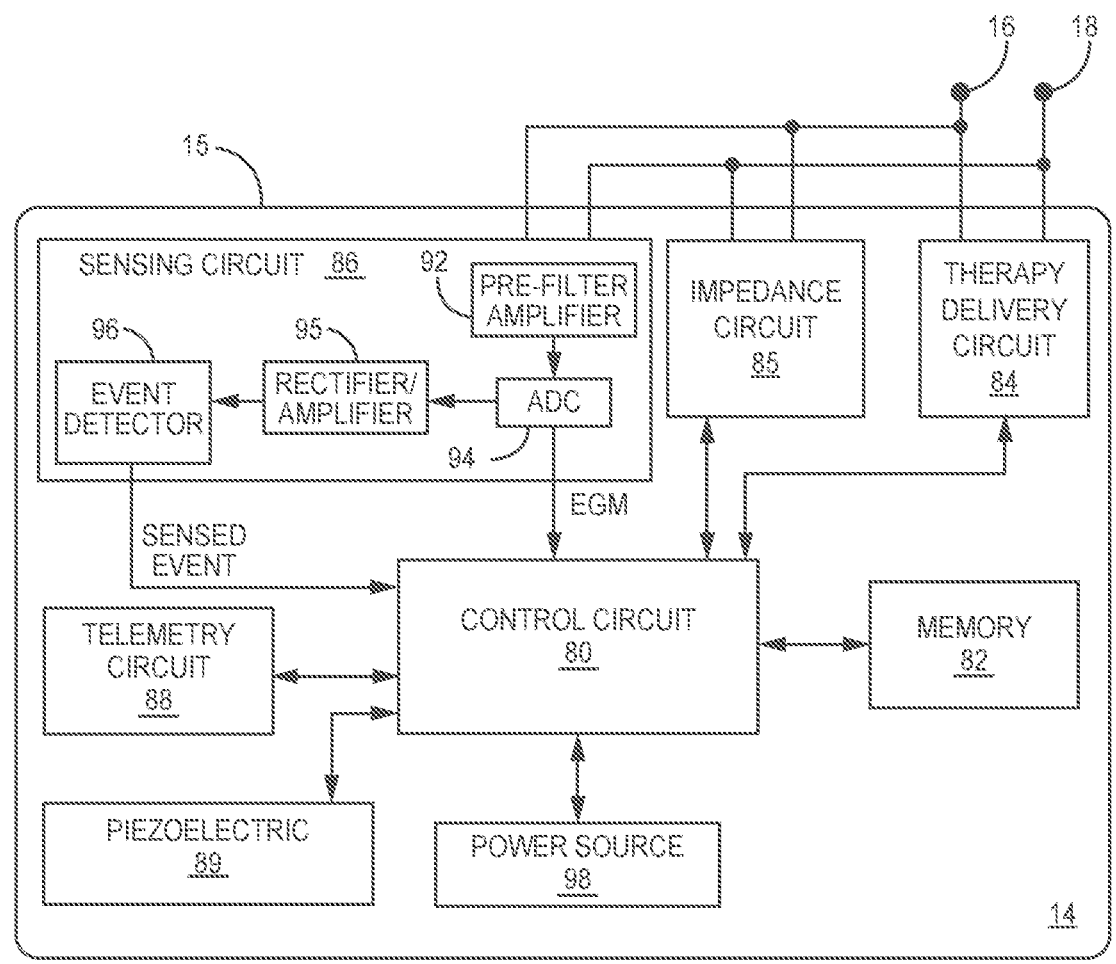
FIG. 4 is a conceptual diagram of circuitry that may be enclosed within an IMD configured to perform cardiac electrical signal sensing and cardiac pacing according to some examples.

FIG. 4 is a conceptual diagram of circuitry that may be enclosed within IMD 14 configured to perform cardiac electrical signal sensing and cardiac pacing according to some examples. The electronic circuitry enclosed within housing 15 includes software, firmware and/or hardware that cooperatively sense and monitor cardiac electrical signals, determine when a pacing therapy is necessary, and deliver electrical pacing pulses to the patient's heart as needed according to programmed pacing mode and pacing pulse control parameters. As described herein, the circuitry may sense a cardiac electrical signal during IMD 14 implantation that may be analyzed by control circuit 80, or transmitted to an external processing circuit, such as processor 52 of external device 50 (FIG. 1), for analysis for detection of a position of the delivery tool distal end face 118 based on a feature (or features) or a change in one or more features of the cardiac electrical signal.

The electronic circuitry included in IMD 14 may include a control circuit 80, memory 82, therapy delivery circuit 84, an impedance circuit 85, sensing circuit 86, telemetry circuit 88 and power source 98. Power source 98 provides power to the circuitry of IMD 14 including each of the circuits 80, 82, 84, 85, 86, and 88 as needed. Power source 98 may include one or more energy storage devices, such as one or more rechargeable or non-rechargeable batteries. Control circuit 80 is powered by power source 98 and may control current delivered to other components of IMD 14 as needed. The connections between power source 98 and each of the other components 82, 84, 85, 86, and 88 are to be understood from the general block diagram of FIG. 4 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for generating and delivering pacing pulses. Power source 98 is also coupled to components of sensing circuit 86 (such as sense amplifiers, analog-to-digital converters, switching circuitry, etc.) as needed to sense a cardiac electrical signal, and to telemetry circuit 88 and memory 82 to provide power to the various circuits as needed.

The functional blocks shown in FIG. 4 represent functionality included in IMD 14 and may include any discrete and/or integrated electronic circuit components that implement analog and/or digital circuits capable of producing the functions attributed to IMD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for sensing cardiac electrical signals and scheduling delivery of cardiac electrical stimulation therapies in response to sensed cardiac events (or the absence thereof), e.g., P-waves attendant to atrial depolarizations when IMD 14 is implanted in an atrial chamber or R-waves attendant to ventricular depolarizations when IMD 14 is implanted in a ventricular chamber. Electrodes 16 and 18 are electrically coupled to therapy delivery circuit 84 for delivering electrical stimulation pulses to the patient's heart and/or to sensing circuit 86 for sensing cardiac electrical signals produced by the heart, which may include both intrinsic signals (such as intrinsic P-waves or R-waves) produced by the heart in the absence of a pacing pulse that captures the heart and evoked response signals produced by the heart in response to a delivered pacing pulse of sufficient energy to cause cardiac capture.

Memory 82 may include computer-readable instructions that, when executed by a processor included in control circuit 80, cause control circuit 80 to perform various functions attributed throughout this disclosure to IMD 14. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 82 may be configured to receive and store an output from control circuit 80 relating to a determined delivery tool position based on cardiac electrical signal analysis performed by control circuit 80. An output stored in memory 82 may be retrieved by control circuit 80 or telemetry circuit 88 for transmission to delivery tool 100 and/or external device 50 for generating a user notification of a determined deployment position of delivery tool 100. A delivery tool deployment position output flag or related data written to memory 82 may be used by control circuit 80 in controlling telemetry circuit 88, piezoelectric element 89, and/or therapy delivery circuit 84 in transmitting or producing a deployment position notification signal that may be detected by delivery tool 100 or external device 50 for use in generating a user notification as disclosed herein.

Sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. In the example shown, sensing circuit 86 includes a pre-filter/amplifier circuit 92 that receives the raw cardiac electrical signal produced by the patient's heart via electrodes 16 and 18. The pre-filter/amplifier circuit 92 may include a relatively wide bandpass filter, for example having a bandpass of 1 to 100 Hz. The filtered and amplified signal is passed to ADC 94, which may pass a digital cardiac electrogram (EGM) signal to control circuit 80. Control circuit 80 may analyze the EGM signal for detecting the position of the delivery tool 100, e.g., detecting abutment between the distal end face 118 of delivery tool 100 and the cardiac tissue. In response to detecting abutment, control circuit 80 may control telemetry circuit 88 to transmit a signal to external device 50 (or delivery tool 100), to generate an output signal by display unit 54 (or user interface 152) notifying an implanting clinician that sufficient contact between the delivery tool and the target implant site has been made for IMD deployment. In other examples, telemetry circuit 88 may transmit the digitized EGM signal received from sensing circuit 86, directly or via control circuit 80, to external device 50 for display to a user via external device display unit 54. Observation of the EGM signal sensed by IMD 14 during advancement of delivery tool 100 may enable the user to determine a deployment position of the delivery tool 100 based on observed features of the EGM signal that correspond to abutment of the distal end face 118 against cardiac tissue. In some examples, external device processor 52 may be configured to process and analyze a received EGM signal for detecting delivery tool position. When sufficient tissue contact is detected, e.g., corresponding to firm, wholly circumferential abutment of distal end face 118 against cardiac tissue based on characteristics of the EGM signal, external device 50 (or delivery tool 100) may generate a notification on display unit 54 (or delivery tool user interface 152) to alert the implanting clinician that IMD 14 may be deployed from the receptacle 110 of delivery tool 100.

Sensing circuit 80 may include a cardiac event detector 96 for detecting intrinsic cardiac events, e.g., P-waves and/or R-waves. The digitized signal from ADC 94 may be rectified and amplified by rectifier/amplifier circuit 95 and passed to cardiac event detector 96. Rectifier/amplifier circuit 95 may include a low pass, bandpass or high pass filter for filtering the cardiac electrical signal over a range of 10 to 60 Hz, for example. In one example, the signal passed to cardiac event detector may be filtered over a range of 15 to 40 Hz or a narrower range with different high and low cut off frequencies. A cardiac event sensing threshold, such as a P-wave sensing threshold or an R-wave sensing threshold, may be automatically adjusted by event detector 96 under the control of control circuit 80, e.g., based on timing intervals and sensing threshold values determined by control circuit 80, stored in memory 82, and/or controlled by hardware, firmware and/or software of control circuit 80 and/or sensing circuit 86. Cardiac event detector 96 senses a cardiac event when the rectified cardiac electrical signal crosses the sensing threshold. Upon sensing a cardiac event based on a sensing threshold crossing, sensing circuit 86 may produce a sensed event signal that is passed to control circuit 80. The sensed event signals produced by sensing circuit 86 are used by control circuit 80 for inhibiting a scheduled pacing pulse and/or for setting pacing escape interval timers that control the basic time intervals used for scheduling cardiac pacing pulses.

Control circuit 80 may include various timers or counters for counting down pacing escape intervals. A sensed event signal may trigger or inhibit a pacing pulse depending on the particular programmed pacing mode. For example, a sensed event signal received from sensing circuit 86 may cause control circuit 80 to inhibit a scheduled pacing pulse and restart the pacing escape interval. If the pacing interval expires before control circuit 80 receives a sensed event signal from sensing circuit 86, control circuit 80 may control therapy delivery circuit 84 to generate and deliver a pacing pulse via electrodes 16 and 18.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse via electrodes 16 and 18 coupled to the therapy delivery circuit 84. Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various pacing modes. Control circuit 80 may also set the amplitude, pulse width, polarity or other characteristics of the cardiac pacing pulses, which may be based on programmed values stored in memory 82.

A medical device configured to perform the techniques disclosed herein may be configured for delivering bradycardia pacing therapy, atrial synchronized ventricular pacing, rate responsive pacing, cardiac resynchronization therapy (CRT), anti-tachycardia pacing therapy or other pacing therapies which may include pacing the atria and/or the ventricles. However, it is to be understood that the techniques disclosed herein may be implemented for detecting the position of a delivery tool being used to deliver and deploy an IMD that does not necessarily include therapy delivery capabilities. In some examples, the IMD may be configured to monitor cardiac signals, e.g., cardiac electrical signals, pressure signals, oxygen saturation, temperature, heart sounds, cardiac motion signals or other cardiac signals. The techniques disclosed herein may be implemented for determining the position of a delivery tool configured to deliver and deploy an IMD at a targeted implant site in or on cardiac tissue.

Control parameters utilized by control circuit 80 for sensing cardiac events and controlling pacing therapy delivery may be programmed into memory 82 via telemetry circuit 88. Telemetry circuit 88 includes a transceiver and antenna for communicating with external device 50 as described above in conjunction with FIG. 1 using radio frequency communication or other communication protocols. Under the control of control circuit 80, telemetry circuit 88 may receive downlink telemetry from and send uplink telemetry to the external device 50. Telemetry circuit 88 may transmit a cardiac electrical signal sensed using electrodes 16 and 18, data derived therefrom and/or an output notification of a detected delivery tool position determined by control circuit 80 based on analysis of the cardiac electrical signal as described below.

Telemetry circuit 88 may include an RF or EM transmitter for generating a telemetry signal that is transmitted by IMD 14 in response to control circuit 80 determining a deployment position of IMD 14 in some examples. The transmitted signal may be detected by sensor 126 included in delivery tool 100. In other examples, the transmitted signal may be received by external device telemetry unit 58. In response to sensing the transmitted signal, the delivery tool 100 may generate a user notification via user interface 152 and/or external device 50 may generate a user notification via display unit 54 to notify the user to deploy the IMD 14.

IMD 14 may include a piezoelectric element 89 that may be driven to transmit a deployment detection signal by vibrating. Control circuit 80 may drive the piezoelectric element 89 to vibrate at specified intervals and/or frequencies by controlling electrical current applied to the piezoelectric element from power source 98. The vibration of the piezoelectric element 89, and subsequent vibration of IMD housing 15, may be sensed by sensor 126 included in delivery tool 100. Upon sensing the vibration signal, sensor 126 may pass a deployment detection signal to sensing and processing circuit 150 for causing user interface 152 to generate a user notification to deploy IMD 14.

In some examples, IMD 14 may include an impedance detection circuit 85, which may be coupled to electrodes 16 and 18 for applying an impedance drive signal to electrodes 16 and 18. The impedance drive signal may be a known current or voltage signal. The resulting impedance signal may be sensed by impedance detection circuit 85. In some examples, a known drive current signal is applied to electrodes 16 and 18 and the resulting voltage signal is sensed by impedance detection circuit 85 using electrodes 16 and 18 as both the drive and recording electrodes. The resulting voltage signal may be determined as an "impedance" signal or converted to an impedance value or signal using the known drive current and the resulting voltage signal by control circuit 80. When other electrodes are available, the drive signal may be applied via one electrode pair and the resulting impedance signal may be sensed using a second recording electrode pair, different than the drive signal electrode pair.

In some examples, control circuit 80 may receive an impedance signal from impedance sensing circuit 85 for use in verifying tissue contact detection made based on the cardiac electrical signal. The impedance between electrodes 16 and 18 may change depending upon the location of receptacle 110 relative to tissue of the target implant site. For example, the electrical impedance may increase when distal end face 118 is proximate to or in direct contact with cardiac tissue compared to the electrical impedance when distal end face 118 is immersed in the heart chamber blood pool or relatively further away from the cardiac tissue.

In some examples, impedance detection circuit 85 may generate an electrical impedance signal by sampling the voltage signal across the electrodes 16 and 18 by a sample and hold circuit included in impedance detection circuit 85. Using this sampled voltage and the known drive current signal, impedance detection circuit 85 may generate an electrical impedance sample point corresponding to the sampled voltage. Impedance detection circuit 85 may sample the voltage signal at a sampling rate that is sufficiently high enough to generate the impedance signal with a resolution that enables detection of an impedance change as the delivery tool distal end face 118 is advanced toward cardiac tissue. For example, impedance detection circuit 85 may sample the voltage signal with a sampling rate around 1000 Hz, though higher or lower sampling rates may be used.

Once impedance detection circuit 85 generates an impedance signal, which may be a sampled voltage signal or an electrical impedance signal determined from the sampled voltage signal, control circuit 80 may determine whether or not the impedance signal indicates that the receptacle 118 is in a deployment position. Control circuit 80 may analyze the "raw" impedance signal in some examples, however, it is to be understood that control circuit 80 may execute one or more operations prior to determining whether or not the impedance signal indicates a deployment position of the delivery tool. For example, control circuit 80 may identify one or more averages, derivatives, or other metrics of the impedance signal to detect a sudden change in the impedance data over time. The use of identifying and analyzing impedance derivative data, for example, may improve an ability of control circuit 80 to detect a deployment position of the delivery tool.

Any technique for determining a metric of electrical impedance between the recording electrodes, e.g., electrodes 16 and 18, may be used for detecting a relative change in impedance due to advancement of the distal end face from immersion in a blood pool to a deployment position against cardiac electrical tissue. Furthermore, while a separate impedance detection circuit 85 is shown in FIG. 4, it is to be understood that the functionality of impedance detection circuit 85 may be implemented in therapy delivery circuit 84, e.g., generating a voltage or current drive signal and recording a resulting signal correlated to the electrical impedance between electrodes 16 and 18. For instance, control circuit 80 may determine a measurement of impedance by controlling therapy delivery circuit 84 to generate a pacing pulse using electrodes 16 and 18 and determining the voltage change on a holding capacitor of therapy delivery circuit 84. The voltage of the holding circuit may be sampled at the beginning and end of the pacing pulse width. The discharge of the holding capacitor during a pacing pulse, from a starting voltage to an ending voltage, is inversely correlated to the electrode impedance. The greater the voltage change, the lower the impedance. A low impedance is associated with immersion in the blood pool of a heart chamber with a higher impedance associated with contact with cardiac tissue. In some examples, control circuit 80 may control telemetry circuit 88 to transmit the impedance signal to external processor 52 of external device 50 for analysis and detection of the delivery tool position. Processing circuitry included in medical device system 10 shown in FIG. 1 may perform impedance determination and identification of a position for delivery tool 100 according to examples generally disclosed in commonly assigned U.S. patent application Ser. No. 16/146,391 (Drake, et al.), incorporated herein by reference in its entirety.

Figure 5:
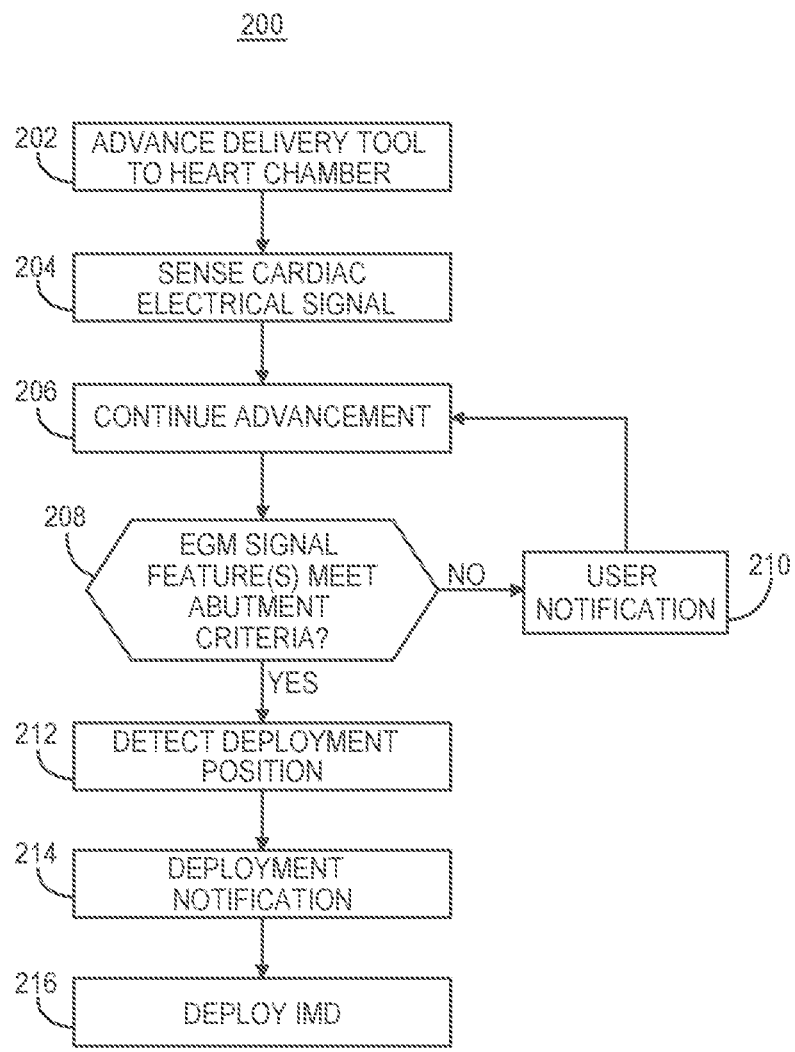
FIG. 5 is a flow chart of a method for detecting a delivery tool position during an IMD implantation procedure according to one example.

FIG. 5 is a flow chart 200 of a method for detecting a delivery tool position during an IMD implantation procedure according to one example. At block 202, the delivery tool 100 is advanced toward a target implant site. As described in conjunction with FIG. 1, the target implant site may be an intracardiac implant site, e.g., within an atrial or ventricular heart chamber. The delivery tool 100 may be advanced transvenously toward the target implant site at block 202.

As the delivery tool 100 is advanced, a cardiac electrical signal is sensed at block 204 by the medical device system. As described above, the cardiac electrical signal may be sensed using first and second electrodes where at least one electrode is located within the receptacle 110 of the delivery tool 100 or along the distal end face 118 of the receptacle 110. When the distal end face 118 is in the blood pool, the relative position of the sensing electrodes to the cardiac tissue results in a cardiac electrical signal having a first set of features. When the distal end face 118 is in light or only partial contact with the cardiac tissue at a target implant site, the proximity of the sensing electrodes to the cardiac tissue may result in the cardiac electrical signal having a second set of features different than the first set of features. After firm, circumferential abutment of the distal end face 118, the cardiac electrical signal may have a third set of features different than the first and second sets of features, due to the more intimal contact of the distal end face 118 with the cardiac tissue. The third set of features of the cardiac electrical signal upon abutment with the cardiac tissue may be associated with a mechanical response of the cardiac tissue upon contact between the distal end face 118 and the cardiac tissue.

Accordingly, detecting one or more features or relative changes in one or more features of the cardiac electrical signal sensed using at least one electrode located within the receptacle 110 or on the receptacle distal end face 118 enables the medical device system to detect a first position of the delivery tool corresponding to immersion of the distal end face 118 in the blood pool, a second position which may correspond to partial or light contact of the distal end face 118 with cardiac tissue, and/or a third position, also referred to herein as the "deployment position," corresponding to firm, wholly circumferential abutment of the distal end face 118 with the cardiac tissue. The first and second positions corresponding to immersion in the blood pool and light or partial contact with the cardiac tissue, respectively, may be referred to as "non-deployment positions" since deployment of the IMD 14 from the receptacle 110 in these positions may result in no engagement with the cardiac tissue or only partial or insufficient engagement with the cardiac tissue by the fixation member 36 at the implant site.

At block 206, the distal end face 118 of delivery tool 100 is advanced toward the target implant site by the user. In some examples, the user may indicate, e.g., via user interface 56, that the delivery tool has entered the targeted cardiac chamber triggering transmission of the sensed cardiac electrical signal from IMD 14 to external device 50, e.g., for display on display unit 54. The user input may start cardiac electrical signal analysis by processing circuitry of the medical device system, e.g., by IMD 14 control circuit 80, by delivery tool processing circuitry 150 or by external device processor 52. The cardiac electrical signal (e.g., an EGM signal generated from the sensed raw cardiac electrical signal) may be monitored at block 208 as continued advancement of the distal end face 118 occurs until at least one feature of the cardiac electrical signal meets criteria for detecting firm, wholly circumferential abutment of the distal end face 118 against the cardiac tissue. Cardiac signal features that may be determined from the cardiac electrical signal for determining if criteria for detecting abutment are met at block 208 are described below in conjunction with FIGS. 6-8. If the cardiac electrical signal does not meet criteria for detecting abutment at block 208, a display unit of the medical device system, e.g., display unit 54 or delivery tool user interface 152, may generate an output at block 210 indicating a non-deployment position of delivery tool 100.

Once criteria for detecting abutment are met at block 208 by one or more cardiac electrical signal features, a deployment position of the delivery tool is determined at block 212, and IMD 14 may be deployed at block 216 by a user interacting with the proximal hub 140 of delivery tool 100. In some examples, the EGM signal is output for storage in memory 82 from control circuit 80 and subsequently transmitted from the IMD 14 to external device 50 and displayed by display unit 54 to a user for determining that the EGM signal meets the abutment criteria based on the display EGM signal. In other examples, a processor of IMD system 10 is configured to detect the deployment position of delivery tool 100 at block 212 based on an analysis of the EGM signal and generate an output at block 214 as a user notification that IMD 14 can be deployed.

In various examples, the control circuit 80 of IMD 14 may determine the deployment position of delivery tool 100 and generate an output signal that may be stored in memory 82, e.g., in RAM of memory 82. The output signal indicating deployment position detection may subsequently cause telemetry circuit 88 and/or piezoelectric element 89 to transmit a user notification signal, e.g., an RF signal, an EM signal, or a vibration, which may be received by delivery tool 100. In other examples, an RF signal may be transmitted by telemetry circuit 88 to external device 50.

A display unit of the medical device system 10, e.g., external device display unit 54 or delivery tool user interface 152, may generate a user notification, e.g., visual, audible, and/or haptic, in response to a transmitted deployment detection signal from IMD 14 to notify the clinician that the deployment position is detected and that IMD 14 may be deployed from the delivery tool 100 (block 214). The output generated at block 214 to notify or prompt a user to deploy IMD 14 may take a variety of forms. In some examples, the output may be a display of a value of a cardiac event signal feature, e.g., the maximum peak amplitude, phase (e.g., monophasic or biphasic), polarity, or signal width. In other examples, the output may be an icon, blinking light, or beeping sound indicating a change in a cardiac event signal feature has been detected that is associated with abutment of the delivery tool distal end face 118 with the cardiac tissue. The output may include a color change of the displayed cardiac electrical signal and/or the value(s) of one or more features derived therefrom. In still other examples, the output may include a display of a textual notification indicating detection of a deployment position of the delivery tool or a notice to deploy.

The user notification generated at block 214 may include a transmitted telemetry signal from IMD telemetry circuit 88. To improve detection of a transmitted telemetry circuit from the IMD 14 by external device 50, the telemetry signal may be a carrier signal that is duty cycled on and off for predetermined time intervals. Due to limited power supply and relatively deep anatomical location of IMD 14, detection of a modulated carrier signal transmitted from IMD 14 by the external device 50 may be unreliable at times. External device telemetry unit 58 may more reliably detect a carrier signal that is cycled on and off. For instance, a detected deployment position notification signal may be transmitted by the IMD telemetry circuit 88 using a carrier signal that is cycled on and off every 5 to 200 milliseconds, as examples. Other time intervals may be selected, however, and the on time may be the same or different than the off time. In other examples, the on time of the duty cycle may be defined by a predetermined number of transmitted carrier signal cycles, each followed by a predetermined off time. The carrier signal may be a 1 kHz to 1,000 kHz signal, 100 to 200 kHz signal, or about 175 kHz center frequency carrier signal, as examples, though other carrier signal frequencies may be used.

In another example, IMD control circuit 80 may generate a deployment position notification at block 214 by controlling therapy delivery circuit 84 to generate pacing pulses. External device 50 may be coupled to surface electrodes for receiving an electrocardiogram (ECG) signal, e.g., via ports 55 (FIG. 1). The ECG signal may be displayed by display unit 54. A pacing artifact appearing in the ECG signal due to the generated pacing pulses may be observed by the clinician as a notification that a deployment position is detected. IMD 14 may be deployed at block 216 upon observing the pacing artifact in the ECG signal. The external device processor 50 may be configured to detect the pacing artifact and generate a user notification for display by display unit 54 and/or via user interface 56. The pacing pulses generated by therapy delivery circuit 84 may or may not cause cardiac capture. The presence of the pacing pulse artifact signal without capture of the heart is sufficient to notify a user that the deployment position of delivery tool 100 is detected by IMD 14. The pacing pulses may be generated by therapy delivery circuit 84 at a predetermined rate, which may be reserved as a distinct rate for deployment notification, such as a rate of 32, 37, 42, 47, 52, 57, 62, 67, 72, as examples with no limitation intended. A pacing rate selected for deployment notification at block 214 may be a rate not typically programmed as a pacing rate or set as a default lower pacing rate in memory 82. In other examples, control circuit 80 may control therapy delivery circuit 84 to generate pacing pulses according to a predetermined pattern of pacing intervals, e.g., successively decreasing intervals, successively increasing intervals, alternating intervals or the like such that external device processor 52 or a user may quickly and reliably identify pacing pulse artifacts in a displayed ECG signal. External device processor 52 may generate an output to memory 53 used in generating an audible, visual or haptic user notification via display unit 54 and/or user interface 56 in response to detecting the pacing pulse artifact.

As another example, in response to the output at block 214, a haptic feedback signal may be generated by IMD 14 and/or by delivery tool 100. As described above, IMD 14 may include a piezoelectric element that may be driven to vibrate by applying an electrical current from power source 98. Vibration of IMD housing 15 may be transferred to the receptacle 110 of delivery tool 100 and either detected by delivery tool sensor 126 and/or the physical vibrations may be transferred along the elongated body 102 of delivery tool 100 to the proximal hub 140. A user may perceive the physical vibrations transferred to the proximal hub 140 as a deployment notification and deploy the IMD at block 216. The ability to transfer physical vibrations along the elongated body 102 (or along the deployment member 130, tether 134, or various electrical conductors extending through the elongated body 102) may depend on the stiffness and material properties of the elongated body and components extending therethrough. The flexibility of the elongated body 102 may prevent transmission of the vibration of IMD housing 15 to the proximal hub 140. In this case, delivery tool 100 may include a sensor 126 for detecting the vibration of IMD 14.

An accelerometer included in delivery tool sensor 126, for example, may produce a motion signal that is conducted to the delivery tool proximal hub 140. The conducted motion signal may be received by sensing and processing circuit 150 and cause processing circuit 150 to control delivery tool user interface 152 to produce an audible, visual or haptic user notification signal indicating deployment position detection, thereby notifying the user to deploy IMD 14. In some examples, the delivery tool user interface 152 may include a piezoelectric element that is driven by a current signal to cause a vibration as a haptic user feedback signal to notify the user that a deployment position is detected and IMD 14 may be deployed.

Delivery tool sensor 126 may include an RF or EM sensor, motion sensor or other sensor configured to sense a deployment detection output signal generated by IMD 14. As described above, the sensor 126 may be coupled to a conductor extending to proximal hub 140 enabling sensing and processing circuit 150 to receive a signal from the sensor 126 and control delivery tool user interface 152 to output an audible, visual or haptic user notification signal indicating that a deployment position is detected.

Figure 6:
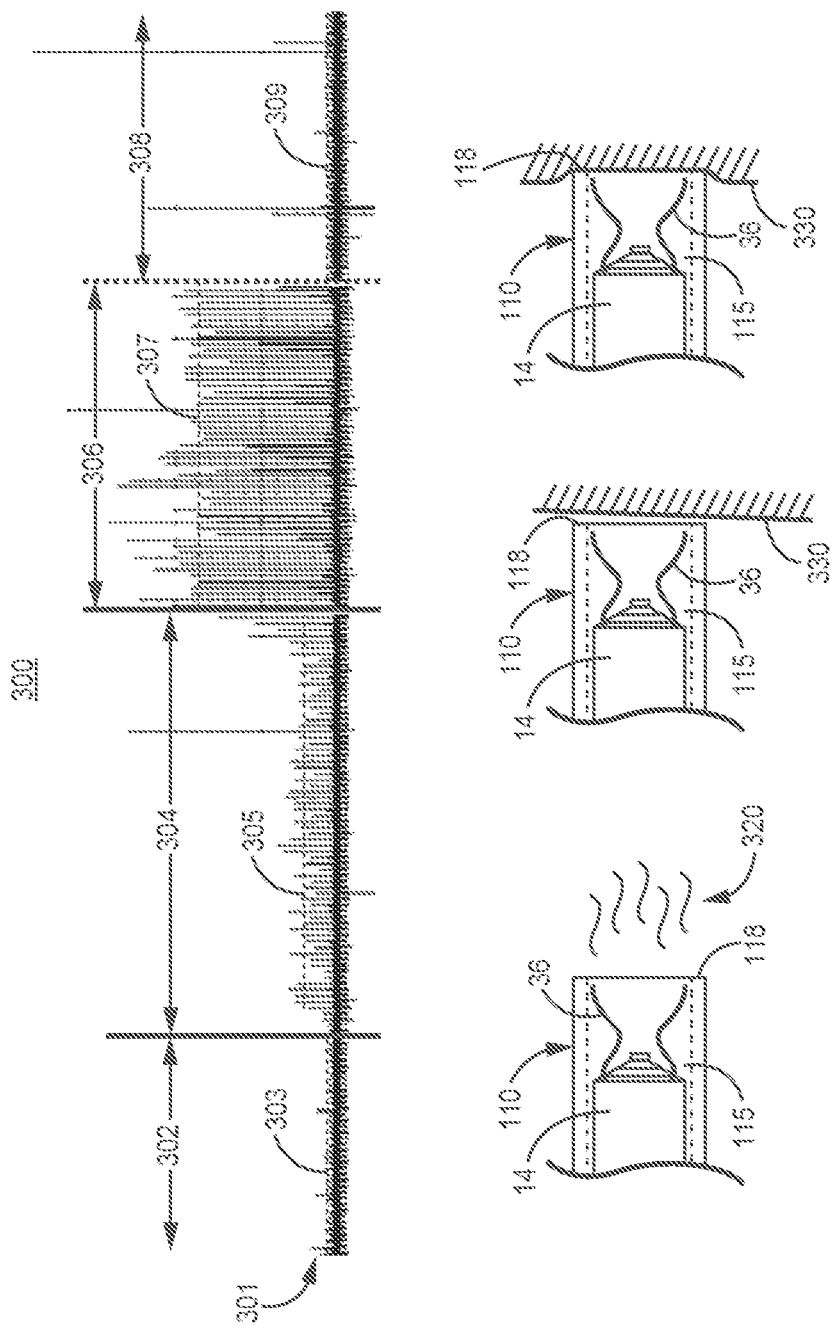
FIG. 6 is a diagram of a cardiac electrical signal that may be received by a processing circuit for use in detecting a position of the delivery tool of FIG. 1 according to one example.

FIG. 6 is a diagram 300 of a cardiac electrical signal 301 that may be received by control circuit 80 from sensing circuit 86 of IMD 14. Signal 301 may be an EGM signal generated by sensing circuit 86 from a raw cardiac electrical signal received via tip electrode 16 and ring electrode 18 of IMD 14, for example. Signal 301 may alternatively be generated by the medical device system from a raw cardiac electrical signal sensed using any of the example combinations of a first electrode contained within the delivery tool receptacle 110 or along its distal end face 118 and a second electrode. Diagram 300 depicts cardiac signal feature changes that may occur with different degrees of contact of the distal end face 118 of delivery tool 100 with cardiac tissue 330 at a target implant site. These cardiac signal feature changes may be detected during advancement of the delivery tool distal end face 118 with IMD 14 retained within the lumen 115 of delivery tool receptacle 110.

In particular, the cardiac electrical signal 301 includes cardiac event signals, e.g., P-waves or R-waves, attendant to the depolarization of the myocardial tissue of the respective atrial or ventricular heart chamber. The maximum peak amplitude of the cardiac event signals changes as the delivery tool distal face 118 is advanced from the heart chamber blood pool to a deployment position. During a first time interval 302, the distal end face 118 of delivery tool 100 remains in the blood pool 320 of a heart chamber. In this example, the delivery tool 100 and IMD 14 may be advanced into the blood pool of the right atrium, such that the cardiac event signals observed in cardiac electrical signal 301 are P-waves. In other instances, the delivery tool distal end face 118 may be advanced into the blood pool of a ventricular chamber such that the cardiac event signals observed in cardiac electrical signal 301 are R-waves. The average maximum peak amplitude 303, of the near field cardiac event signals when distal end face 118 is immersed in blood pool 320 is indicated by dashed line and is relatively low.

During a second time interval 304, the distal end face 118 of delivery tool 100 makes light or partial contact with the cardiac tissue 330 at a target implant site. The average maximum peak amplitude 305, indicated by dashed line, of the cardiac event signals may increase when the distal end face 118 makes light or partial contact with the cardiac tissue. However, this degree of contact may be insufficient to achieve acceptable fixation of all tines of fixation member 36. For example, light contact may not allow all tines of fixation member 36 to penetrate or engage the cardiac tissue deeply enough to promote secure fixation of the IMD 14 at the implant site. In some instances, incomplete or partial abutment of distal end face 118 may occur when the distal end face 118 is angled relative to the surface of the cardiac tissue 330. In this case only some of the tines of fixation member 36, instead of all of the tines, may engage with the cardiac tissue 330 upon deployment of IMD 14 out of receptacle 110. In other instances, all tines of fixation member 36 may penetrate and engage with the cardiac tissue 330 but the penetration of at least some of the fixation member tines may be too shallow in the cardiac tissue to sufficiently engage the tissue for secure, chronic fixation of IMD 14. Furthermore, sufficient engagement of all tines of the fixation member 36, distal tip electrode 16 may be poorly coupled to the cardiac tissue, potentially resulting in poor or intermittent cardiac tissue contact in the beating heart, high pacing capture thresholds and/or relatively low cardiac signal strength and potential undersensing of cardiac events.

When distal end face 118 makes only light, partial or intermittent circumferential contact with cardiac tissue 330, an increase in the cardiac event amplitude 305 may be detected compared to the cardiac event amplitude 303 during blood pool immersion. This intermediate cardiac event amplitude 305, however, does not meet criteria for detecting a deployment position corresponding to firm, wholly circumferential abutment of the distal end face 118 against the cardiac tissue 330. The relatively low amplitude cardiac event signal amplitudes 303 and 305 therefore correspond to non-deployment positions of the delivery tool 100.

During the third time interval 306, the cardiac event average maximum amplitude 307, indicated by dashed line, is significantly greater than the average maximum amplitude 305 during partial or light tissue contact and the average maximum amplitude 303 during immersion in the blood pool 320. The high amplitude cardiac event signals during time interval 306 indicate that distal end face 118 is tightly abutted against the cardiac tissue 330, e.g., making wholly circumferential contact with the cardiac tissue along distal end face 118. When the cardiac event signal amplitude exceeds a threshold amplitude, which may be determined by a user based on the visual representation of cardiac electrical signal 301 on external device display unit 54 or as detected by processing circuitry of the medical device system (e.g., by control circuit 80 of IMD 14, external device processor 52, or delivery tool sensing and processing circuit 150), a deployment position of delivery tool 100 corresponding to abutment of the delivery tool distal end face 118 against cardiac tissue 330 is detected. The threshold amplitude of cardiac event signals (e.g., P-waves or R-waves) for detecting the deployment position may be predefined or based on the cardiac event signal amplitude 303 during immersion in the blood pool 320 and/or the cardiac event signal amplitude 305 during light or partial contact with cardiac tissue 330. For example, the cardiac event amplitude 307 may be required to be a predetermined percentage increase over the amplitude 303 or amplitude 305 in order for deployment position detection criteria to be met. Deployment of fixation member 36 when the cardiac event amplitude is determined to increase significantly from the blood pool amplitude 303 or light contact amplitude 305 is expected to allow all fixation member tines to sufficiently engage with the cardiac tissue 330 at the implant site, securely coupling the IMD distal tip electrode 16 with the cardiac tissue 330.

The maximum peak amplitude 307 upon reaching firm, wholly circumferential abutment may depend on the cardiac wall thickness at the site of contact. A relatively high maximum peak amplitude 307 may indicate a relatively thicker portion of the heart chamber wall at the point of contact. A relatively low maximum peak amplitude 307 may indicate a relatively thinner portion of the heart chamber wall. A low maximum peak amplitude or disappearance of the cardiac event signals may indicate a necrotic or fibrous portion of the heart chamber wall that is not a desirable deployment site due to impaired cardiac sensing and pacing at that site. Depending on the desired penetration depth of fixation member 36 and other material and structural properties of the fixation member tines, a desirable deployment site may be a site where the heart chamber wall is not a relatively thick portion or fibrous portion. In other instances, the desirable deployment site may be a site that is not a relatively thin portion, to avoid penetration of the heart wall by fixation member 36 or dislodgement of fixation member 36. As such, in some examples, the increased maximum peak amplitude 307 may be compared to a threshold range that corresponds to desirable heart chamber wall thickness (and viability) for determining a deployment position of the delivery tool 100. The comparison of maximum peak amplitude 307 to a threshold range may be visually represented on display of the cardiac electrical signal 301 on external device display unit 54 or performed by a processor of IMD 14, delivery tool 100 or external device 50.

In some examples, a processor of the medical device system 10 (e.g., external device processor 52, delivery tool sensing and processing circuit 150, or IMD control circuit 80) may determine the average peak amplitudes 303, 305 and 307. The processor may output the average peak amplitudes to a memory so that an increased peak amplitude may be compared to the stored average peak amplitudes or to a threshold range. The solid or dashed lines 303, 305 and 307 may be generated for display by external device display unit 54 to indicate the change in average peak amplitude and thereby prompt the user to determine the deployment position of the delivery tool 100 and deliver IMD 14. The numerical values of the average peak amplitudes may additionally or alternatively be displayed. In some examples, the output generated by a processor of the system 10 may include a color change of the cardiac electrical signal 301 displayed on external device display unit 54, a color change of the line indicating the average peak amplitude, and/or a color change of a displayed peak amplitude numerical value, e.g., from red during low amplitude 303, to yellow when a first increase to amplitude 305 is detected and/or to green when the second, larger increase to amplitude 307 is detected.

During the fourth time interval 308, contact between the cardiac tissue and distal end face 118 of the delivery tool 100 is lost. The cardiac event average peak amplitude 309, indicated by dashed line, decreases dramatically. Distal end face 118 may be immersed in the blood pool again as shown during first time interval 302. Accordingly, during the implant procedure, a processor of the medical device system may output data for displaying a decrease in cardiac event peak amplitude and/or detect a decrease in the peak amplitude and output a non-deployment position detection signal. When a decrease in the average peak amplitude is displayed or detected, the external device display unit 54 or delivery tool interface 152 may generate a user notification that a non-deployment position of the delivery tool is detected, and IMD 14 should not be deployed (if not already deployed). This drop in cardiac event signal amplitude may occur if the delivery tool 100 is moved or shifted away from the cardiac tissue during the implant procedure, before IMD deployment.

It is to be understood that external device processor 52 may receive transmitted EGM signal data from IMD 14 and generate output to memory 53 for subsequent use by display unit 54 in displaying visual representations of the EGM signal and changes in features of the EGM signal that occur as delivery tool 100 is advanced into a deployment position. For example, the diagram of cardiac electrical signal 301 shown in FIG. 6, and the other diagrams of cardiac electrical signals presented herein, may be displayed in a graphical user interface (GUI) on external device display unit 54 as a visual representation of a cardiac electrical signal and changing cardiac event signal features representative of changing locations of delivery tool distal face 118 as it is advanced to an implant site. In the particular example shown in FIG. 6, the displayed cardiac electrical signal 301 includes changing maximum peak amplitudes 303, 305 and 307 of cardiac event signals that represents to a user the changing location of the delivery tool distal end face 118 relative to cardiac tissue. A user may interact with the GUI to save or freeze a cardiac electrical signal episode, zoom in or out on the cardiac electrical signal to view signal features, mark a peak amplitude location, or the like to enable the user to determine a deployment position of the delivery tool 100 based on displayed cardiac electrical signal features.

Figure 7:
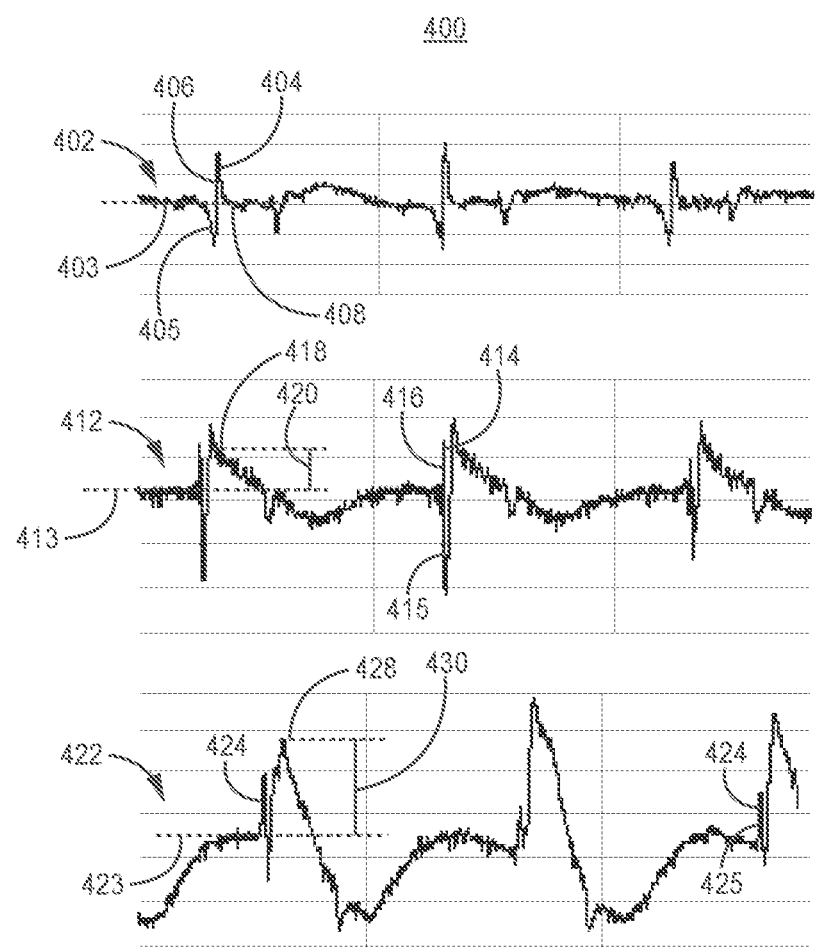
FIG. 7 is a diagram of cardiac electrical signal features that may exist during advancement of a delivery tool distal end face into an atrial blood pool, into light or partial contact with the cardiac tissue, and upon firm abutment with the cardiac tissue according to another example.

FIG. 7 is a diagram 400 of cardiac electrical signal features that may exist during advancement of the delivery tool distal end face 118 into an atrial blood pool, into light or partial contact with the cardiac tissue, and upon firm abutment with the cardiac tissue according to another example. The top cardiac electrical signal 402 may be received by processing circuitry of the medical device system 10, e.g., via electrodes 16 and 18 (or other selected first and second electrodes), when the delivery tool distal end face 118 is within the atrial blood pool. The P-wave 404 is biphasic having a negative-going portion 405 and a positive-going portion 406. The cardiac electrical signal 402 returns to a baseline amplitude 408 after P-wave 404. The baseline amplitude 408 is approximately equal to the baseline amplitude 403 prior to P-wave 404.

The middle cardiac electrical signal 412 may be received by processing circuitry of the medical device system 10 after further advancement of distal end face 118, upon making light or partial contact with the cardiac tissue. The P-wave 414 is still a biphasic signal in this example, with a negative-going portion 415 and a positive-going portion 416. The baseline amplitude 418 after the P-wave 414 is elevated from the baseline amplitude 413 prior to the P-wave, indicating an injury current associated with contact with the cardiac tissue. The difference 420 between the baseline amplitude 413 preceding the P-wave and the baseline amplitude 418 subsequent to the P-wave may be compared to an injury current threshold difference for detecting contact between delivery tool distal end face 118 and cardiac tissue.

The bottom cardiac electrical signal 422 may be received by processing circuitry of the medical device system 10 upon firm abutment of the distal end face 118 against the cardiac tissue, with wholly circumferential contact between distal end face 118 and the cardiac tissue. The P-wave 424 is substantially a monophasic signal with primarily a positive-going portion 425 in this example and minimal or absent negative-going portion. The baseline amplitude 428 after the P-wave 424 is elevated significantly from the baseline amplitude 423 prior to the P-wave 424, indicating an increased injury current upon firm abutment of the delivery tool distal end face 118 against cardiac tissue. The injury current represented by baseline amplitude difference 430 is greater than the amplitude difference 420 observed in signal 412 upon relatively lighter or partial contact. The difference 430 between the baseline amplitude 423 preceding the P-wave 424 and the baseline amplitude 428 subsequent to the P-wave may be compared to an injury current threshold difference for detecting abutment between delivery tool distal end face 118 and cardiac tissue. The injury current threshold difference for detecting abutment may be a predetermined threshold difference or based on detecting a relative increase in the post-P-wave baseline amplitude 428 compared to the post-P-wave baseline amplitude 418 when light or partial contact is made.

Abutment of delivery tool distal end face 118 against the cardiac tissue may additionally or alternatively be detected based on detecting a monophasic cardiac event signal or the change from a biphasic to a monophasic cardiac event signal. For example, a processor of medical device system 10 (e.g., IMD control circuit 80, external device processor 52 and/or delivery tool sensing and processing circuit 150) receiving the cardiac electrical signal may perform P-wave morphology analysis or detect a minimum peak amplitude of the P-wave to detect a monophasic P-wave 424 or the change from a biphasic P-wave 406 and 414 to a monophasic P-wave 424. While the example cardiac electrical signals and associated signal features shown in FIG. 7 are atrial signals and atrial signal features (e.g., P-wave morphology and injury current), it is to be understood that a post-R-wave injury current and/or a change in R-wave morphology from biphasic to monophasic may be detected from a ventricular signal when delivery tool distal end face 118 is advanced into a ventricular heart chamber. A deployment position of the delivery tool 100 may be determined in response to detecting an increased injury current based on the pre- to post-cardiac event signal baseline amplitude and/or the change from a biphasic to monophasic cardiac event signal morphology.

Figure 8:
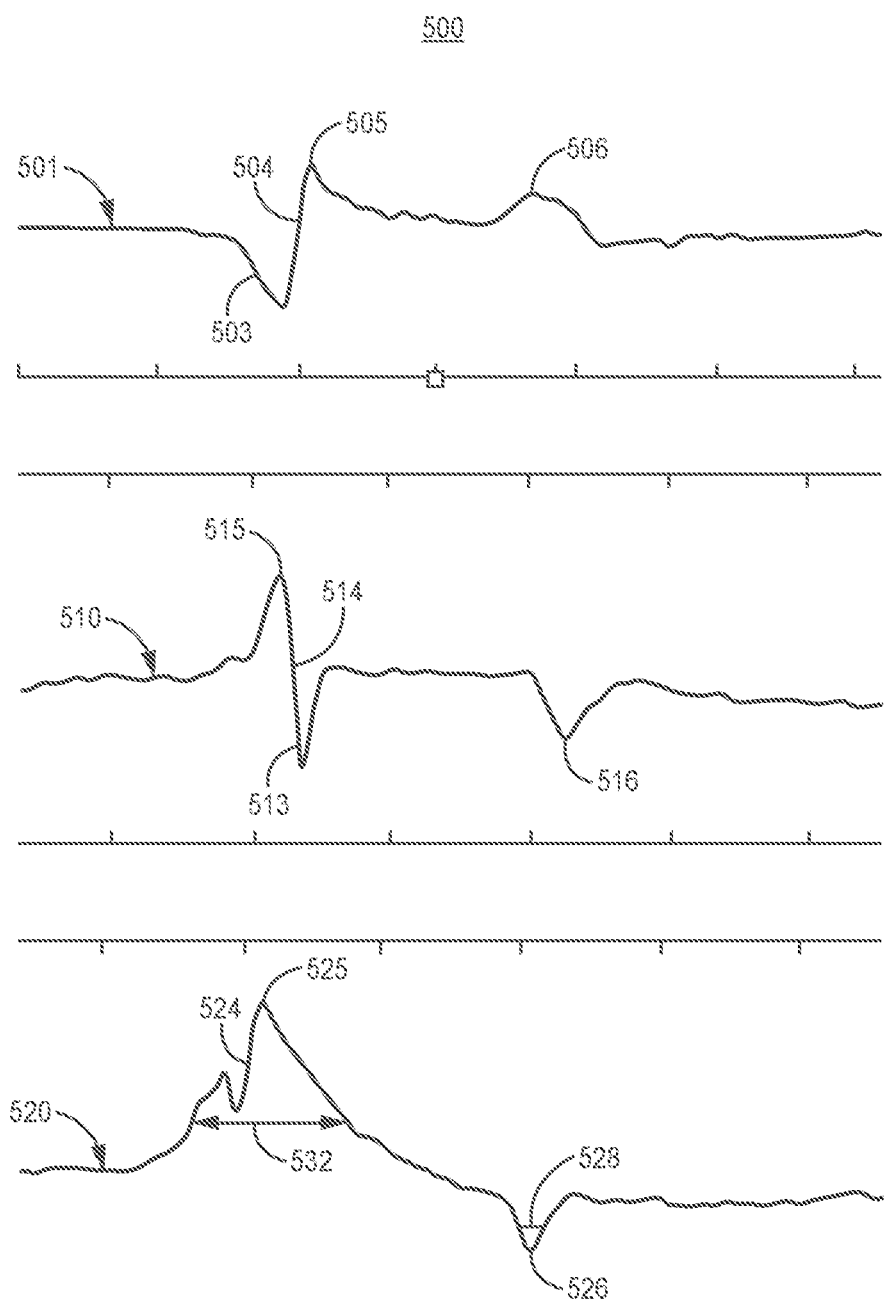
FIG. 8 is a diagram of cardiac electrical signals, which may be received by processing circuitry of the medical device system of FIG. 1, when the delivery tool distal end face is within the atrial blood pool, in contact with the cardiac tissue, and fully abutting the cardiac tissue.

FIG. 8 is a diagram 500 of cardiac electrical signals, which may be received by processing circuitry of the medical device system 10 when the delivery tool distal end face 118 is within the atrial blood pool (signal 501), in contact with the cardiac tissue (signal 510) and fully abutting the cardiac tissue (signal 520) in a deployment position. In this example, the delivery tool distal end face 118 is advanced into the atrial blood pool at which point P-wave 504 of signal 501 is biphasic, having a negative-going portion 503 and a positive-going portion 505. Upon making light or partial cardiac tissue contact with the delivery tool distal end face 118, the P-wave 514 of signal 510, remains biphasic having a negative-going portion 513 and a positive-going portion but has an increased maximum peak amplitude 515 compared to maximum peak amplitude 505 of the P-wave 504 during blood pool immersion of distal end face 118. The positive-going portion 515 leads the negative-going portion 513 upon light tissue contact by distal end face 118 in contrast to the negative-going portion 503 leading the positive-going portion 505 in signal 501 when distal end face 118 is immersed in the blood pool. These signal changes, an increased maximum peak amplitude and the change in P-wave morphology, may be detected by a processor of IMD 14, delivery tool 100 or external device 50 as an indication that tissue contact has been made by the distal end face 118. The EGM signal exhibiting these signal changes may be displayed by external device display unit 54 for presentation to a user as a representation of delivery tool distal end face 118 advancement from the blood pool to tissue contact.

With further advancement of delivery tool distal end face 118 against the cardiac tissue, a processor of the medical device system 10 may receive signal 520 including P-wave 524 which is monophasic (only positive-going in this example), having a relatively high maximum peak amplitude 525 and a signal width 532 that is wider than the widths of the positive portion of either of the P-waves 504 and 514. A cardiac event signal width, in this example the P-wave width 532, may be determined as the time from the maximum peak amplitude 525 to a predetermined percentage of the peak amplitude 525 before and/or after the peak amplitude 525, e.g., the time from the peak amplitude 525 to 10% of the maximum peak amplitude. The time interval before and the time interval after the maximum peak amplitude 525 to the predetermined percentage of the maximum peak amplitude 525 may be summed to determine the P-wave width 532. In other examples, the P-wave width may be determined based on the time interval from a maximum positive slew rate to the maximum peak amplitude, from the maximum positive slew rate to a maximum negative slew rate, or from the maximum peak amplitude to the maximum negative slew rate. In still other examples, the P-wave width 532 may be determined as the time interval from a positive going threshold crossing to a negative going threshold crossing. A metric of P-wave width 532 may be determined according to a variety of techniques to provide a comparable value for detecting an increase in P-wave width (of at least the positive going portion) as the delivery tool 100 is advanced. The processing circuitry of the medical device system 10, e.g., IMD control circuit 80, delivery tool sensing and processing circuit 150, or external device processor 52, may determine and detect a P-wave signal width greater than a signal width threshold or detect a relative increase in the P-wave signal width during advancement of delivery tool 100 as an indication of abutment of the delivery tool distal end face 118 against cardiac tissue.

In some cases, a far-field R-wave (FFRW) may be present in the cardiac electrical signals 501, 510 and 520 acquired from within the atrial chamber. In the example shown, the FFRW 506 of atrial blood pool signal 501 has a positive polarity. However, once light or partial cardiac tissue contact is made by delivery tool distal end face 118, the FFRW 516 of signal 510 may reverse polarity to be a negative-going signal. When delivery tool distal end face 118 is firmly abutted against the cardiac tissue in a deployment position, the FFRW 526 of signal 520 remains negative in polarity and may have a minimum peak amplitude and/or a signal width 528 that is different than the magnitude (absolute value) and/or width of FFRW 516 received during relatively lighter contact with the cardiac tissue. Techniques described above for determining a cardiac event width may be used for determining the FFRW width 528. A negative polarity FFRW or a change in the polarity of the FFRW may be detected by the medical device system processing circuitry as criteria for detecting abutment of the distal end face 118 of the delivery tool against the cardiac tissue.

The examples of FIG. 8 refer to changes in P-waves and FFRWs when the delivery tool distal end face 118 is within an atrial chamber for atrial deployment of IMD 14. However, analogous changes may occur in R-waves, and far field P-waves if present in the cardiac electrical signal, when the delivery tool distal end face 118 is advanced into a ventricular chamber for ventricular deployment of IMD 14. For instance, the R-wave may change from a biphasic to a monophasic signal having a higher peak amplitude and wider signal width as the distal end face 118 is advanced from the ventricular blood pool to firm abutment against the cardiac tissue. A far-field P-wave, if present in the ventricular signal, may change polarity, increase in amplitude, and/or increase in signal width.

In various examples, a maximum or minimum peak amplitude, peak positive and/or negative slope, maximum peak-to-peak amplitude, signal width, signal area (e.g., integration or summation of sample points), signal polarity, signal morphology being monophasic or biphasic, or other feature or any combination of features may be determined from a cardiac event signal (e.g., a near field P-wave and/or far-field R-wave during implantation in an atrial chamber or a near field R-wave and/or far field P-wave during implantation in a ventricular chamber). The cardiac event signal feature or combination of features may be determined beat by beat or less often as the distal end face 118 of delivery tool 100 is advanced from within a heart chamber blood pool to a position against cardiac tissue at a target implant site to enable detection of at least one cardiac event signal feature, e.g., a monophasic morphology, and/or detection of a relative change in at least one feature, e.g., a relative increase in maximum peak amplitude or a relative increase in signal width, corresponding to wholly circumferential abutment of the distal end face 118 against the cardiac tissue in a deployment position of delivery tool 100.

The examples of cardiac electrical signal changes described in conjunction with FIGS. 6-8 may be detected by IMD control circuit 80, by external device processor 52, by delivery tool sensing and processing circuit 150 or cooperatively by any combination of processing circuitry included in IMD control circuit 80, processor 52 and/or sensing and processing circuit 150. In some examples the cardiac electrical signal received by control circuit 80 may be transmitted to processor 52 for processing, analysis and detection of cardiac signal changes indicative of abutment (and a deployment position) of delivery tool distal end face 118 against the cardiac tissue. In other examples, IMD control circuit 80 may analyze the cardiac signal to determine cardiac signal feature values, e.g., cardiac event peak amplitude, polarity, signal width, and/or phase (monophasic vs. biphasic) of the near field cardiac event signal (P-wave or R-wave) attendant to depolarization within the same heart chamber as the delivery tool distal end face 118 is in (atrial or ventricular) and/or of the far field cardiac event signal (R-wave or P-wave) attendant to depolarization in the adjacent chamber (ventricular or atrial). One or a combination of cardiac signal features may be determined and compared to deployment position detection criteria by control circuit 80 or transmitted to external device 50 for comparison to deployment position detection criteria. In some examples, a display of the cardiac electrical signal, derived cardiac electrical signal feature values, results of comparisons to deployment position detection criteria, and/or a user notification based on the comparison to deployment position detection criteria may be generated by external device display unit 54.

External device processor 52 may output data to memory 53 for use by display unit 54 in generating a display of the EGM signal received from IMD 14 or delivery tool 100 sensed using at least one electrode enclosed within receptacle 110 or located on distal end face 118. Display unit 54 may include a graphical user interface and be configured to display the EGM signal transmitted from IMD 14 (or delivery tool 100) to external device 50 providing a visual representation of the cardiac electrical signal changes as the user advances the delivery tool 100 through a heart chamber, against cardiac tissue and into a deployment position corresponding to wholly circumferential, firm abutment of the distal end face 118. The visual representation of the signal changes described above in a GUI enables a user to determine the deployment position of the delivery tool 100 and deploy IMD 14 in response to reliably determining the deployment position.

Figure 9:
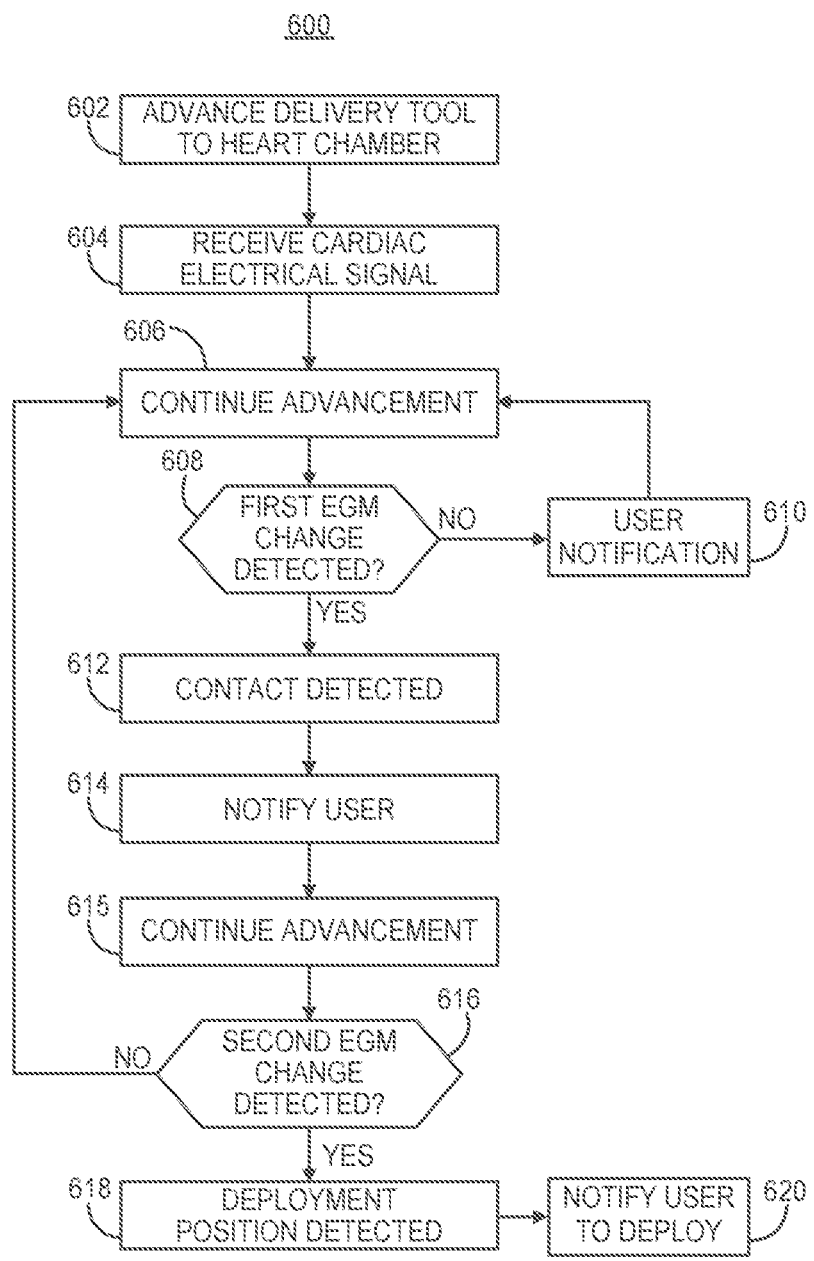
FIG. 9 is a flow chart of a method for detecting a position of a delivery tool during advancement to a target implant site according to another example.

FIG. 9 is a flow chart 600 of a method for detecting a position of delivery tool 100 during advancement to a target implant site according to another example. As described in conjunction with FIG. 5, the delivery tool distal end face 118 is advanced into a desired heart chamber at block 602. In some examples, a user may provide an input via user interface 56 indicating that the delivery tool 100 has entered the targeted heart chamber at block 602, to trigger the medical device system to initiate the process of sensing a cardiac electrical signal using an electrode within receptacle 110 (or on distal face 118), displaying the sensed electrical signal on display unit 54 and/or analyzing cardiac electrical signal features for determining delivery tool position. In other examples, the IMD 14 and/or delivery tool 100 may begin sensing and analyzing and/or transmitting the cardiac electrical signal without requiring user input. The cardiac electrical signal is sensed at block 604, e.g., by IMD sensing circuit 86 using distal tip electrode 16 and ring electrode 18, or by sensing and processing circuit 150 of delivery tool 100 using a first electrode within receptacle 110, e.g., IMD ring electrode 18 or electrode 122, or an electrode 119 on distal end face 118 (see FIGS. 3A and 3B) paired with a second electrode selected from any of the available electrodes on delivery tool 100 (e.g., electrode 120) or a cutaneous or subcutaneously-placed indifferent electrode. Initially, the near field cardiac event signals (e.g., P-waves or R-waves) of the cardiac electrical signal, may be relatively low amplitude, narrow, biphasic cardiac event signals as described above. A far field cardiac event signal (e.g., far field R-wave or far field P-wave), if present in the sensed cardiac signal may have an initial polarity, e.g., positive polarity, and be relatively low amplitude. One or more near field cardiac event signal features and/or far field cardiac event signal features may be determined at block 604 for use in detecting a change in the signal feature(s) indicative of advancement from within the blood pool to firm abutment against cardiac tissue corresponding to a deployment position.

At block 606, the distal end face 118 of the delivery tool 100, with IMD 14 retained within receptacle 110, is advanced toward a target implant site. The target implant site may be within the atrial appendage, along the atrial endocardial wall, or along the ventricular wall. The cardiac electrical signal is monitored at block 608 to detect a first change in one or more signal features indicative of advancement of the distal end face 118 from immersion in the blood pool to tissue contact by distal end face 118. As described in conjunction with FIGS. 6-8, the first cardiac electrical signal change detected at block 608 may include a first threshold (or relative) increase in peak amplitude of the cardiac event signal, detection of an injury current based on a first threshold increase in the baseline amplitude after the cardiac event signal, and/or a change in polarity of the far field cardiac event signal. If the first change in the cardiac electrical signal is not detected ("no" branch of block 608), a display unit of the medical device system 10 may generate a user notification at block 610 to indicate a delivery tool position corresponding to blood pool immersion, a non-deployment position of the delivery tool and/or a prompt to continue advancing the delivery tool distal end.

Upon detecting the first change in the cardiac electrical signal indicative of tissue contact being made by distal end face 118 ("yes" branch of block 608), the processing circuitry of medical device system 10 may detect tissue contact by the delivery tool distal end face 118 at block 612. A user notification may be generated at block 614. The user notification may be generated by external display unit 54 or delivery tool user interface 152 according to any of the example visual, audible or haptic notification techniques given above indicating that tissue contact has been made and/or prompting the user to advance or apply greater forward pressure to delivery tool 100 at block 615 to achieve a deployment position. In some examples, the tissue contact of distal end face 118 is visually represented by external device display unit 54, e.g., by displaying and/or highlighting the EGM signal received from IMD 14 (or delivery tool 100) including the cardiac event signal change corresponding to tissue contact by delivery tool distal end face 118.

At block 616, cardiac electrical signal features are determined by processing circuitry of medical device system 10 and/or displayed in a cardiac electrical signal to enable detection of a second change in the cardiac electrical signal indicative of firm abutment of the delivery tool distal end face 118 against cardiac tissue. Abutment may be detected at block 618 in response to a second threshold increase in the cardiac event amplitude (greater than the first threshold increase), a threshold increase in the cardiac event signal width, a change from a biphasic cardiac event signal to a monophasic cardiac event signal and/or a second threshold increase in the post-cardiac event baseline amplitude indicating a larger injury current or any combination thereof. In some examples, the cardiac event amplitude falling within a threshold range corresponding to a desired heart wall thickness is determined as a second EGM signal change at bock 616 indicating a deployment position determination.

When a second cardiac electrical signal change is not detected at block 616, the processing circuitry continues to monitor and/or display the cardiac electrical signal for detecting abutment and determining a deployment position. In some cases, initial tissue contact may be detected then lost resulting in the first cardiac electrical signal change no longer being detected at block 608. Furthermore, it is recognized that in some cases, the second cardiac electrical signal change may be detected without detecting the first signal change at block 608, e.g., when the distal end is advanced rapidly against the cardiac tissue site. As such, simultaneous monitoring for cardiac signal features corresponding to non-deployment and deployment positions of the delivery tool may be ongoing until the IMD 14 is deployed. Once a deployment position is detected at block 618, based on cardiac event signal criteria being met, a user notification may be generated by external device display unit 54 and/or delivery tool user interface 152 at block 620 to notify the user of the detection of the deployment position of delivery tool 100 and/or prompt the user to deploy IMD 14 by advancing IMD 14 out of the delivery tool receptacle 110, e.g., to engage the cardiac tissue with all tines of fixation member 36. In this way, a medical device system including processing circuitry configured to receive a cardiac electrical signal may generate an output to a memory for subsequent display of a visual representation of a cardiac electrical signal (or features thereof) corresponding to one or more non-deployment positions and/or a deployment position of a medical device delivery tool during advancement to a target implant site. Additionally or alternatively, the processing circuitry may be configured to perform cardiac signal analysis to detect one or more non-deployment positions and/or a deployment position of a medical device delivery tool during advancement to a target implant site based on an analysis of the cardiac electrical signal features.

Figure 10:
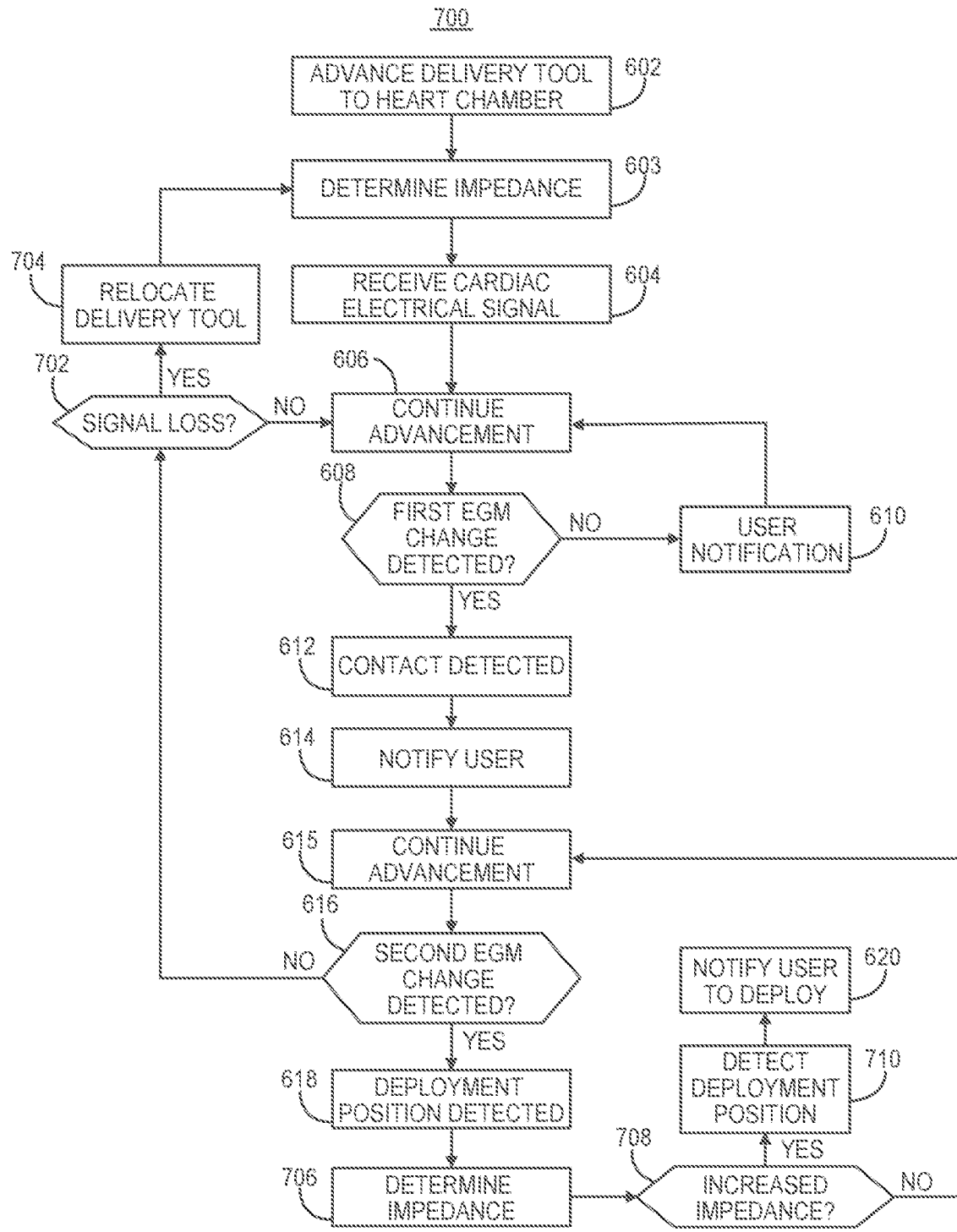
FIG. 10 is a flow chart of a method for detecting a deployment position of a delivery tool by a medical device system according to another example.

FIG. 10 is a flow chart 700 of a method for detecting a deployment position of a delivery tool by a medical device system according to another example. Identical reference numbers shown in FIG. 10 correspond to like-numbered blocks described above in conjunction with FIG. 9. As described above, the delivery tool 100 is advanced into a targeted heart chamber at block 602. A user may input a command or signal via delivery tool 100 or external user interface 56 that the distal receptacle is positioned in the targeted heart chamber so that IMD 14 and/or delivery tool 100 can begin acquiring electrical signals needed to detect the deployment position of delivery tool 100. In this example, both a cardiac electrical signal (e.g., EGM signal) and an electrical impedance signal may be used for determining the delivery tool position.

At block 603, the impedance detection circuit 85 may generate an impedance signal so that control circuit 80 can determine a starting impedance, e.g., corresponding to immersion of the delivery tool distal end face 118 in the heart chamber blood pool. At block 604, processing circuitry, e.g., control circuit 80 of IMD 14 may receive a cardiac electrical signal from sensing circuit 86. In some examples, one or more features of the cardiac electrical signal corresponding to the position in the blood pool may be determined by processing circuitry of the medical device system 10. As the delivery tool 100 is advanced further toward the target implant site, the processing circuitry of the medical device system 10 may determine the cardiac electrical signal feature(s). If no change in the cardiac electrical signal feature(s) is(are) detected, the system may generate a user notification to continue advancement of the delivery tool at block 606. When the first change in the cardiac electrical signal is detected, at block 608, indicating that contact with the cardiac tissue has been detected (block 612), the medical device system 10 may generate an output (block 614) indicating that contact with cardiac tissue is detected and to continue slowly applying a forward pressure (block 615) to achieve a deployment position. The output may be a predetermined color of a light emitting diode (e.g., green to yellow light), decreased frequency or increased volume of an audible beep, and/or a text or voiced notice on display unit 54, as examples.

At block 616, processing circuitry of medical device system 10 operates to display and/or analyze the cardiac electrical signal for visually representing and/or detecting a second change indicative of abutment of the distal end face 118 against the cardiac tissue. In some cases, the cardiac electrical signal may be lost (e.g., a large decrease in amplitude or a relatively flat baseline signal with very low amplitude fluctuations) or otherwise significantly altered due to abutment against necrotic or non-viable cardiac tissue. When the second cardiac electrical signal change indicative of abutment of distal end face 118 against the target implant site is not detected, the processing circuitry may detect a change indicating cardiac electrical signal loss associated with a non-viable tissue site (block 702). Cardiac electrical signal loss may be detected at block 702 based on a loss of cardiac event sensing based on a sensing threshold crossing by the cardiac electrical signal (e.g., by sensing circuit 86), a decrease in the average maximum peak amplitude of the cardiac electrical signal to less than a percentage of a previously detected maximum peak amplitude, e.g., less than 20% of the peak amplitude determined upon contact with cardiac tissue or less than 50% of the peak amplitude determined during immersion of the distal end face 118 in the blood pool. Additionally or alternatively, signal loss may be detected at block 702 based on a threshold or percentage decrease in the cardiac event signal width and/or cardiac event signal area compared to a previously determined signal width and/or signal area upon detecting a non-deployment position of the delivery tool 100. When loss of signal is detected, the medical device system 10 may be configured to generate an output to notify the user that the implant site is unacceptable and/or to relocate the delivery tool (block 704).

The user may retract the delivery tool 100 and advance toward a new target implant site. The baseline impedance determined in the heart chamber blood pool may optionally be redetermined at block 603 prior to advancing toward the new site. If the second change in the cardiac electrical signal indicative of abutment is not detected at block 616, but a signal loss indicative of non-viable tissue is not detected at block 702, the delivery tool 100 may be advanced further at block 606 until the second cardiac electrical signal change indicative of abutment of distal end face 118 against the target implant site is detected.

When abutment is detected at block 618 based on one or more features of the cardiac electrical signal, processing circuitry of the medical device system may determine the impedance at block 706 to verify wholly circumferential abutment of the distal end face 118 against the target implant site. In some cases, the criteria for detecting abutment based on the cardiac electrical signal may be satisfied when the distal end face 118 is actually positioned at a slight angle relative to the tissue surface. The impedance signal may be analyzed to verify the deployment position.

The impedance determined at block 706 may be compared to the impedance determined at block 603 to determine if a threshold impedance increase is detected at block 708. In one example, if at least a ten percent increase in impedance is detected (block 708) compared to the impedance determined prior to detecting abutment based on the cardiac electrical signal, the deployment position of the delivery tool 100 is detected at block 710. A user operating delivery tool 100 may determine a deployment position based on the visual representation of the cardiac electrical signal displayed on external device display unit 54 and in response to an electrode impedance value transmitted from IMD 14 to external device processor 52 (for display on display unit 54) and/or a deployment position detection signal from IMD 14 based on an impedance measurement confirming an expected electrode impedance between electrodes 16 and 18. The user may deploy IMD 14 in response to the deployment position determination. An output signal may be generated by display unit 54 and/or delivery tool user interface 152 at block 620 notifying the user that the delivery tool 100 may be in an acceptable position for IMD deployment and that the IMD 14 may be deployed at the target implant site.

Accordingly, in some examples, criteria for detecting a deployment position of the delivery tool 100 may include a required change in at least one feature of the cardiac electrical signal and a threshold or percentage increase in electrical impedance measured between a recording pair of electrodes. The order in which the cardiac electrical signal feature(s) and the electrical impedance are determined and verified to meet deployment position detection may vary from the particular order shown in FIG. 10.

Figure 11:
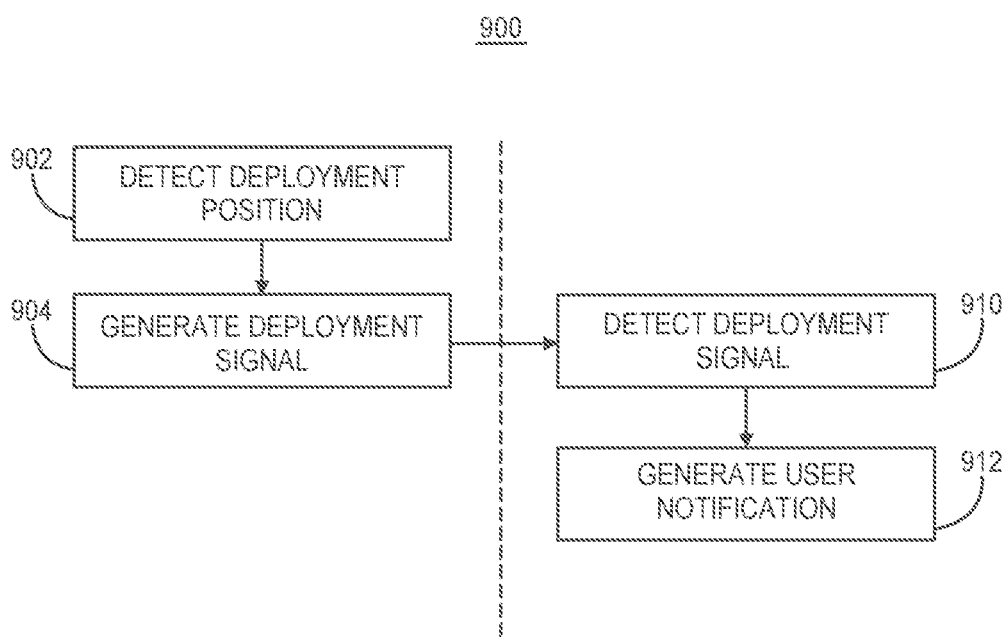
FIG. 11 is a flow chart 900 of a method for generating a deployment notification to a user by a medical device system according to some examples.

FIG. 11 is a flow chart 900 of a method for generating a deployment notification to a user by a medical device system according to some examples. Blocks 902 and 904 on the left side of the dashed line represent operations that may be performed by IMD 14. Blocks 910 and 912 on the right side of the dashed line represent operations that may be performed by delivery tool 100. At block 902, IMD control circuit 80 detects a deployment position of delivery tool 100 using any of the techniques disclosed herein, which may include an analysis of a sensed EGM signal and determining an electrode impedance.

At block 904, control circuit 80 generates a deployment position notification signal in response to detecting the deployment position. The deployment position notification signal may be generated in a variety of forms and in some examples more than one deployment position notification signal may be generated to affirm detection and recognition by a user that the delivery tool 100 is in position for pacemaker deployment. In one example, IMD control circuit 80 generates the deployment position notification signal by controlling telemetry circuit 88 to transmit a signal, which may be an RF or EM signal as examples. The transmitted signal may be received at block 910 by sensor 126 included in delivery tool 100, which may be incorporated in the receptacle 110, along elongated body 102 or in the proximal hub 140 such that the energy required to transmit the deployment position notification signal by IMD telemetry circuit 88 may be reduced relative to transmitting a signal to external device 50. In other examples, the transmitted signal may be a carrier signal that is cycled on and off according to a predetermined duty cycle by IMD telemetry circuit 88.

The duty cycled carrier signal may be more easily detected at block 910 by a receiver included in delivery tool 100 or external device telemetry unit 58 than a modulated carrier signal.

In other examples, control circuit 80 generates the deployment position notification signal by applying a current signal to the piezoelectric element 89 to cause a vibration. Piezoelectric element 89 may be driven to vibrate in a repeated, pulsed manner, for example, and consequently cause vibration of the pacemaker housing 15. In some examples, the vibration of the IMD 14 within receptacle 110 may be transferred along the elongated body 102 (or an elongated member such as a conductor or deployment member 130 extending through elongated body 102) to proximal hub 140. A user may perceive the vibration as a haptic feedback signal indicating that delivery tool 100 is in a deployment position. In other examples, sensor 126 may include an accelerometer included in receptacle 110 or along the distal portion of elongated body 102. Sensor 126 may produce an acceleration signal responsive to the vibration of pacemaker housing 15. The acceleration signal may be received by delivery tool sensing and processing circuit 150. Sensing and processing circuit 150 may be configured to detect the acceleration signal corresponding to a deployment position notification signal generated by IMD 14. For instance, the vibrational signal produced by the IMD piezoelectric element 89 may be generated according to a predefined pattern or duty cycle that causes the delivery tool sensor 126 to produce a corresponding signal that is detectable by sensing and processing circuit 150 as a deployment position notification signal. Sensing and processing circuit 150 may in turn generate a user feedback signal at block 912, which may include any audible, visual or haptic user feedback signal generated by proximal hub 140 or by external device 50 in response to detecting a deployment position notification signal transmitted by delivery tool 100.

In still other examples, IMD control circuit 80 may be configured to control therapy delivery circuit 84 to generate pacing pulses at block 904 as a deployment position notification signal. The pacing pulses may be generated at a predetermined rate, interval, pulse number or other specified parameters as a predetermined deployment position notification signal. Delivery tool processing circuit 150 or external device processor 52 may detect the pacing pulses from a sensed EGM or ECG signal. In other examples, the appearance of the pacing artifact corresponding to the pacing pulses generated by IMD 14 may be displayed in an ECG signal received via external ports 55 by processor 52 and stored in memory 53 for generating a display by display unit 54. A user may observe the pacing pulse artifacts in the ECG signal as the user notification signal to deploy IMD 14.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device system.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the terms "processor" or "processing circuitry" as used herein may refer to any of the foregoing structure or any other structure suitable for implementation of the techniques described herein. Also, the techniques could be fully implemented in one or more circuits or logic elements.

Thus, a medical device system for delivering an IMD to a targeted implant site has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system, comprising:
    a delivery tool having a distal end face, the delivery tool configured to deploy an implantable medical device (IMD) at an implant site, the delivery tool configured to retain the IMD as the distal end face of the delivery tool is advanced to the implant site;
    a memory configured to store:
        first criteria for detecting contact of the distal end face of the delivery tool with adjacent tissue at the implant site, the first criteria comprising at least a first injury current threshold; and
        second criteria for detecting firm circumferential abutment of the distal end face of the delivery tool against the adjacent tissue at the implant site prior to deployment of the IMD, the second criteria comprising at least a second injury current threshold that is different than the first injury current threshold; and
    a processor configured to:
        receive a cardiac electrical signal sensed by a sensing electrode pair when at least a first electrode of the sensing electrode pair is retained within the delivery tool, the cardiac electrical signal comprising cardiac event signals attendant to depolarizations of cardiac tissue;
        determine at least a first feature of the cardiac electrical signal;
        determine that the first feature meets the second injury current threshold of the second criteria for detecting a deployment position of the delivery tool, the deployment position corresponding to the firm circumferential abutment of the distal end face of the delivery tool with adjacent tissue at the implant site prior to deployment of the IMD; and
        generate an output in response to detecting the deployment position; and
    the memory further configured to store the output.

2. The medical device system of claim 1, further comprising cardiac electrical signal sensing circuitry configured to sense the cardiac electrical signal via the sensing electrode pair comprising at least the first electrode that is retained within the delivery tool when the received cardiac electrical signal is sensed.

3. The medical device system of claim 1, wherein the processor is configured to:
    detect a first change in the cardiac electrical signal sensed during advancement of the delivery tool to the implant site that meets the first injury current threshold stored in the memory;
    detect a non-deployment position of the delivery tool in response to detecting the first change;
    detect a second change in the cardiac electrical signal after detecting the first change, the second change meeting the second criteria stored in the memory; and
    detect the deployment position of the delivery tool in response to the second criteria being met.

4. The medical device system of claim 1, wherein the processor is configured to:
    determine at least a second feature from the sensed cardiac electrical signal by determining a peak amplitude of a cardiac event signal that is attendant to the depolarization of the cardiac tissue; and
    determine that the peak amplitude meets the second criteria for detecting the deployment position.

5. The medical device system of claim 4, wherein the processor is configured to determine that the peak amplitude meets position detection by determining that the peak amplitude of the cardiac event signal that is attendant to the depolarization of the cardiac tissue is within a peak amplitude threshold range.

6. The medical device system of claim 1, wherein the processor is configured to:
    determine at least a second feature by determining a polarity of a far field cardiac event signal of the cardiac electrical signal; and
    determine that the second feature meets the second criteria for detecting the deployment position by detecting a reversal of the polarity of the far field cardiac event signal.

7. The medical device system of claim 1, wherein the processor is configured to:
    determine at least a second feature of the cardiac electrical signal by determining a phase of a cardiac event signal that is attendant to the depolarization of the cardiac tissue as being monophasic; and
    determine that the second feature meets the second criteria for detecting the deployment position by determining that the cardiac event signal that is attendant to the depolarization of the cardiac tissue is monophasic.

8. The medical device system of claim 1, wherein the processor is configured to:
    determine at least a second feature of the cardiac electrical signal by determining a signal width of a cardiac event signal that is attendant to the depolarization of the cardiac tissue; and
    determine that the signal width meets the second criteria for detecting the deployment position.

9. The medical device system of claim 1, wherein the processor is configured to:
    determine the first feature by determining a baseline amplitude after a cardiac event signal of the cardiac electrical signal; and determine that the baseline amplitude after the cardiac event signal meets the second criteria for detecting the deployment position.

10. The medical device system of claim 1, wherein the processor is further configured to:
receive an impedance signal;
determine that the impedance signal meets deployment position impedance criteria; and
generate the output in response to determining that the first feature meets the second criteria for detecting the deployment position and the impedance signal meeting the deployment position impedance criteria.

11. The medical device system of claim 1, further comprising a telemetry circuit configured to transmit a deployment position detection signal in response to the output stored in the memory.

12. The medical device system of claim 11, wherein the telemetry circuit is configured to transmit the deployment position detection signal as a duty cycled carrier signal.

13. The medical device system of claim 1, further comprising a therapy delivery circuit configured to generate a plurality of pacing pulses in response to the generated output.

14. The medical device system of claim 1, further comprising a piezoelectric element configured to generate a vibration signal in response to the generated output.

15. The medical device system of claim 1, further comprising a display unit configured to display a visual representation of the received cardiac electrical signal.

16. The medical device system of claim 1, further comprising a user interface configured to output a user notification in response to the output generated by the processor.

17. The medical device system of claim 1, wherein:
the delivery tool further comprises:
a receptacle for retaining the IMD; and
a distal opening of the receptacle, the distal end face of the delivery tool being a circumferential distal end face defining the distal opening of the receptacle; and
the processor being further configured to determine that the first feature of the cardiac electrical signal meets the second criteria for detecting the deployment position of the delivery tool by determining that the first feature meets criteria for detecting wholly circumferential abutment of the circumferential distal end face of the delivery tool with the adjacent tissue.

18. The medical device system of claim 1 further comprising the sensing electrode pair comprising the first electrode and a second electrode both retained within the delivery tool prior to deployment of the IMD when the delivery tool is in the non-deployment position and in the deployment position.

19. A method, comprising:
storing in a medical device system memory:
first criteria for detecting contact of a distal end face of a delivery tool with adjacent tissue at an implant site, the first criteria comprising at least a first injury current threshold; and
second criteria for detecting firm circumferential abutment of the distal end face of the delivery tool against the adjacent tissue at the implant site prior to deployment of an IMD retained by the delivery tool, the second criteria comprising at least a second injury current threshold that is different than the first injury current threshold;
receiving a cardiac electrical signal sensed by a sensing electrode pair when at least a first electrode of the sensing electrode pair is retained within the delivery tool, the cardiac electrical signal comprising cardiac event signals attendant to depolarizations of cardiac tissue;
determining at least a first feature of the cardiac electrical signal;
determining that the first feature meets the second injury current threshold of the second criteria for detecting a deployment position of the delivery tool the deployment position corresponding to the firm circumferential abutment of the distal end face of the delivery tool with the adjacent tissue at the implant site prior to deployment of the IMD; and
deploying the IMD from the delivery tool in response to determining that at least the second injury current threshold of the second criteria is met.

20. The method of claim 19, further comprising:
detecting a first change in the cardiac electrical signal sensed during advancement of the delivery tool to the implant site that meets the first injury current threshold;
detecting a non-deployment position of the delivery tool in response to detecting the first change;
detecting a second change in the cardiac electrical signal after detecting the first change, the second change meeting the second criteria; and
detecting a the deployment position of the delivery tool in response to the second criteria being met.

21. The method of claim 19, comprising:
determining at least a second feature of the sensed cardiac electrical signal by determining a peak amplitude of a cardiac event signal that is attendant to the depolarization of the cardiac tissue; and
determining that the peak amplitude meets the second criteria for detecting the deployment position.

22. The method of claim 21, wherein determining that the peak amplitude meets the second criteria for detecting the deployment position comprises determining that the peak amplitude of the cardiac event signal that is attendant to the depolarization of the cardiac tissue is within a peak amplitude threshold range.

23. The method of claim 19, comprising:
determining at least a second feature by determining a polarity of a far field cardiac event signal of the cardiac electrical signal; and
determining that the second feature meets the second criteria for detecting the deployment position by detecting a reversal of the polarity of the far field cardiac event signal as the delivery tool is advanced.

24. The method of claim 19, comprising:
determining at least a second feature of the cardiac electrical signal by determining a phase of a cardiac event signal that is attendant to the depolarization of the cardiac tissue as being monophasic; and
determining that the second feature meets the second criteria for detecting the deployment position by determining that the cardiac event signal that is attendant to the depolarization of the cardiac tissue is the monophasic.

25. The method of claim 19, comprising:
determining at least a second feature of the cardiac electrical signal by determining a signal width of a cardiac event signal that is attendant to the depolarization of the cardiac tissue; and
determining that the signal width meets the second criteria for detecting the deployment position.

26. The method of claim 19, comprising:
determining the first feature by determining a baseline amplitude after a cardiac event signal of the cardiac electrical signal; and
determining that the baseline amplitude after the cardiac event signal meets the second criteria for detecting the deployment position.

27. The method of claim 19, further comprising:
determining that an impedance signal meets deployment position impedance criteria; and
deploying the IMD from the delivery tool in response to determining that the second criteria for detecting the deployment position and the deployment position impedance criteria are met.

28. An implantable medical device system, comprising:
a memory configured to store:
  first criteria for detecting contact of a distal end face of a delivery tool with adjacent tissue at an implant site, the first criteria comprising at least a first injury current threshold; and
  second criteria for detecting firm circumferential abutment of the distal end face of the delivery tool against the adjacent tissue at the implant site prior to deployment of an implantable medical device (IMD) retained by the delivery tool, the second criteria comprising at least a second injury current threshold that is different than the first injury current threshold; and
a processor configured to:
  receive a cardiac electrical signal comprising cardiac event signals attendant to depolarizations of cardiac tissue;
  determine that the cardiac electrical signal meets the second injury current threshold;
  based on at least the cardiac electrical signal meeting the second injury current threshold, detect a deployment position of the delivery tool corresponding to the firm circumferential abutment of the distal end face of the delivery tool against the adjacent tissue at the implant site prior to deployment of the IMD; and
  generate an output based on the cardiac electrical signal meeting the second injury current threshold; and
a display unit configured to, in response to the output, generate a visual representation of changes in the cardiac event signals attendant to depolarizations of the cardiac tissue as the delivery tool is advanced to the deployment position, the delivery tool being configured to retain the (IMD) as the delivery tool is advanced to the implant site and configured to deploy the IMD at the implant site.

* * * * *